(12) United States Patent
Singh et al.

(10) Patent No.: US 9,827,224 B2
(45) Date of Patent: *Nov. 28, 2017

(54) METHODS AND COMPOSITIONS FOR AMELIORATING PANCREATIC CANCER

(71) Applicant: University of South Alabama, Mobile, AL (US)

(72) Inventors: Seema Singh, Mobile, AL (US); Ajay P. Singh, Mobile, AL (US)

(73) Assignee: University of South Alabama, Mobile, AL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/007,002

(22) Filed: Jan. 26, 2016

(65) Prior Publication Data
US 2016/0220532 A1    Aug. 4, 2016

Related U.S. Application Data

(63) Continuation of application No. 13/881,695, filed as application No. PCT/US2011/057751 on Oct. 25, 2011, now Pat. No. 9,267,934.

(60) Provisional application No. 61/455,795, filed on Oct. 26, 2010.

(51) Int. Cl.
| | |
|---|---|
| *A61K 31/395* | (2006.01) |
| *G01N 33/50* | (2006.01) |
| *A61K 31/7088* | (2006.01) |
| *A61K 31/7105* | (2006.01) |
| *C12N 15/113* | (2010.01) |

(52) U.S. Cl.
CPC ........ *A61K 31/395* (2013.01); *A61K 31/7088* (2013.01); *A61K 31/7105* (2013.01); *C12N 15/1138* (2013.01); *G01N 33/502* (2013.01); *C12N 2310/14* (2013.01)

(58) Field of Classification Search
None
See application file for complete search history.

(56) References Cited

U.S. PATENT DOCUMENTS

| | | | |
|---|---|---|---|
| 7,423,007 B2 | 9/2008 | Fujii et al. | |
| 9,155,723 B2 * | 10/2015 | Jain .................. | A61K 45/06 |
| 9,267,934 B2 | 2/2016 | Singh et al. | |
| 2004/0132642 A1 | 7/2004 | Hwang | |
| 2007/0160574 A1 | 7/2007 | Merzouk et al. | |
| 2010/0184694 A1 | 7/2010 | Peled et al. | |
| 2010/0222256 A1 | 9/2010 | Fujii | |
| 2011/0281814 A1 | 11/2011 | Dash et al. | |
| 2013/0171105 A1 | 7/2013 | Blackman et al. | |
| 2013/0216531 A1 | 8/2013 | Jain et al. | |
| 2013/0281423 A1 | 10/2013 | Singh et al. | |

FOREIGN PATENT DOCUMENTS

| | | |
|---|---|---|
| WO | WO 2001/076615 | 10/2001 |
| WO | WO 2001/085196 | 11/2001 |
| WO | WO 2002/094261 | 11/2002 |
| WO | WO2004/087065 | * 10/2004 |
| WO | WO 2006/095542 | 9/2006 |

OTHER PUBLICATIONS

Lapteva, et al. (2005) CXCR4 knockdown by small interfering RNA abrogates breast tumor growth in vivo. Cancer Gene Therapy, v.12:84-9.*
Marchesi, et al. (2004) Increased Survival, Proliferation, and Migration in Metastatic Human Pancreatic Tumor Cells Expressing Functional CXCR4. Cancer Research, v.64:8420-7.*
Hermann, et al. (2007) Distinct Populations of Cancer Stem Cells Determine Tumor Growth and Metastatic Activity in Human Pancreatic Cancer. Cell Stem Cell, v.1:313-23.*
Deer, et al. (2010) Phenotype and Genotype of Pancreatic Cancer Cell Lines. Pancreas, v.39(4):425-35.*
Azab el al., CXCR4 inhibitor AMD3100 disrupts the interaction of multiple myeloma cells with the bone marrow microenvironment and enhances their sensitivity to therapy. Blood (2009) 113(18): 4341-4351.
Bai et al., Akt-mediated regulation of NFkappaB and the essentialness of NFkappaB for the oncogenicity of PI3K and Akt, Int J Cancer. (2009) 125(12): 2863-2870.
Balabanian et al., The Chemokine SDF-1/CXCL12 binds to and signals through the orphan receptor RDC1 in T lymphocytes, J Biol Chem. (2005); 280: 35760-35766.
Calegari et al., Tissue-specific RNA interference in postimplantation mouse embryos with endoribonuclease-prepared short interfering RNA, Proc. Natl. Acad. Sci. USA. (2002) 99(22): 14236-14240.
Chae et al., Requirement for sphingosine 1-phosphate receptor-1 in tumor angiogenesis demonstrated by in vivo RNA interference, J Clin Invest. (2004) 114(8): 1082-1089.
Chiu et al., RNAi in Human Cells: Basic Structural and Functional Features of Small Interfering RNA, Mol Cell. (2002) 10: 549-561.
Clackson et al. Making antibody fragments using phage display libraries, Nature (1991) 352: 624-628.
Datta et al., Akt phosphorylation of BAD couples survival signals to the cell-intrinsic deatch machinery, Cell (1997) 91(2): 231-241.
De Clercq E. The bicyclam AMD3100 story, Nat Rev Drug Discov. (2003) 2(7): 581-587.
de Fougerolles et al., RNA Interference In Vivo: Toward Synthetic Small Inhibitory RNA-based Therapeutics, Methods Enzymol. (2005) 392: 278-296.

(Continued)

*Primary Examiner* — Jennifer Pitrak McDonald
(74) *Attorney, Agent, or Firm* — Knobbe, Martens, Olson & Bear, LLP

(57) ABSTRACT

Embodiments of the present invention include methods and compositions for ameliorating cancer. Some embodiments include methods and compositions for ameliorating pancreatic cancer targeting the CXCR4 receptor and the CXCL12 ligand.

16 Claims, 10 Drawing Sheets

(56) References Cited

OTHER PUBLICATIONS

Devine et al., Rapid mobilization of CD34+ cells following administration of the CXCR4 antagonist AMD3100 to patients with multiple myeloma and non-Hodgkin's lymphoma, J Clin Oncol. (2004) 22(6): 1095-1102.

Elbashir et al. Duplexes of 21—nucleotide RNAs mediate RNA interference in cultured mammalian cells, Nature (2001) 411: 494-498.

Faber et al., The Many Facets of SDF-1alpha, CXCR4 Agonists and Antagonists on Hematopoietic Progenitor Cells, J Biomed Biotechnol. (2007) 2007: 26065; 10 pages.

Fang et al., Phosphorylation of beta-catenin by AKT promotes beta-catenin transcriptional activity. J Bio Chem. (2007) 282(15): 11221-11229.

Fuchs et al. Silencing of Disease-related Genes by Small Interfering RNAs, Curr Mol Med. (2004) 4: 507-517.

Gelmini et al., The critical role of SDF-1/CXCR4 axis in cancer and cancer stem cells metastasis, J Endocrinol Invest. (2008) 31(9): 809-819.

Gibson et al., A novel method for real time quantitative RT-PCR, Genome Res. (1996) 10: 995-1001.

Glodek et al., Focal adhesion kinase is required for CXCL12-induced chemotactic and pro-adhesive responses in hematopoietic precursor cells, Leukemia (2007) 21(8): 1723-1732.

Gupta et al., Inducible, reversible, and stable RNA interference in mammalian cells, PNAS (2004) 101(7): 1927-1932.

Harikumar et al., Resveratrol, a multitargeted agent, can enhance antitumor activity of gemcitabine in vitro and in orthotopic mouse model of human pancreatic cancer, Int J Cancer. (2010) 127(2): 257-268.

Heid et al., Real time quantitative PCR, Genome Res. (1996) 6: 986-994.

Hermann et al., Distinct populations of cancer stem cells determine tumor growth and metastatic activity in human pancreatic cancer, Cell Stem Cell (2007) 1(3): 313-323.

Huanwen et al., Intrinsic chemoresistance to gemcitabine is associated with constitutive and laminin-induced phosphorylation of FAK in pancreatic cancer cell lines, Mol Cancer (2009) 8: 125.

Hutvágner et al., RNAi: nature abhors a double-strand, Curr. Opin. Genet. Dev. (2002) 12:225232.

Ichim et al., RNA Interference: A Potent Tool for Gene-Specific Therapeutics, Am J Transplant (2004) 4:1227-1236.

Jana et al., RNA interference: potential therapeutic targets, Appl Microbiol Biotech. (2004) 65: 649-657.

Jemal et al., Cancer Statistics, CA Cancer J Clin, (2009) 59(4): 225-249.

Ji et al., EGF-induced ERK activation promotes CK2-mediated disassociation of alpha-Catenin from beta-Catenin and transactivation of beta-Catenin, Mol Cell (2009) 36(4): 547-559.

Jiang et al., Gel-based Application of siRNA to Human Epithelial Cancer Cells Induces RNAi-dependent Apoptosis, Oligonucleotides (2004) 14(4): 239-248.

Korkaya et al., Regulation of mammary stem/progenitor cells by PTEN/Akt/beta-catenin signaling, PLoS Biol. (2009) 7(6): e1000121; 15 pages.

Koshiba et al., Expression of stromal cell-derived factor 1 and CXCR4 ligand receptor system in pancreatic cancer: a possible role for tumor progression, Clin Cancer Res. (2000) 6(9): 3530-3535.

Lee et al., Expression of small interfering RNAs targeted against HIV-1 rev transcripts in human cells. Nature Biotechnol. (2002) 20: 500-505.

Lewis D. L. Efficient delivery of siRNA for inhibition of gene expression in postnatal mice, Nature Genetics (2002) 32: 107-108.

Li et al., Up-regulation of *miR-200* and *let-7* by natural agents leads to the reversal of epithelial-to-mesenchymal transition in gemcitabine-resistant pancreatic cancer cells, Cancer Res. (2009) 69(16): 6704-6712.

Liang et al., Inhibition of breast cancer metastasis by selective synthetic polypeptide against CXCR4, Cancer Res. (2004) 64(12): 4302-4308.

Liau et al., HMGA1 is a molecular determinant of chemoresistance to gemcitabine in pancreatic adenocarcinoma. Clin Cancer Res. (2008) 14(5): 1470-1477.

Lu et al., SDF-1alpha up-regulates interleukin-6 through CXCR4, PI3K/Akt, ERK, and NF-kappaB-dependent pathway in microglia, Eur J Pharmacol. (2009) 613(1-3): 146-154.

Madrid et al., Akt suppresses apoptosis by stimulating the transactivation potential of the RelA/p65 subunit of NF-kappaB, Mol Cell Biol. (2000) 20(5): 1626-1638.

Maréchal et al., High expression of CXCR4 may predict poor survival in resected pancreatic adenocarcinoma,. Br J Cancer (2009) 100(9): 1444-1451.

Marchesi et al., Increased survival, proliferation, and migration in metastatic human pancreatic tumor cells expressing functional CXCR4, Cancer Res. (Nov. 2004); 64(22): 8420-8427.

Marlow et al., SLITs suppress tumor growth in vivo by silencing Sdf1/Cxcr4 within breast epithelium, Cancer Res (2008) 68(19): 7819-7827.

Matsuo et al., CXCL8/IL-8 and CXCL12/SDF-1alpha co-operatively promote invasiveness and angiogenesis in pancreatic cancer, Int J Cancer (2009) 124(4): 853-861.

McIntyre et al., Design and cloning strategies for constructing shRNA expression vectors; BMC Biotechnol. (2006) 6: 1; 8 pages.

McManus et al. Gene Silencing Using Micro-RNA Designated Hairpins, RNA (2002) 8: 842-850.

Middleton et al., New treatment options for advanced pancreatic cancer. Expert Rev Gastroenterol Hepatol. (2008) 2(5): 673-696.

Miyagishi et al., U6 promoter—driven siRNAs with four uridine 3' overhangs efficiently suppress targeted gene expression in mammalian cells, Nat Biotechnol. (2002) 20: 497-500.

Monick et al., Lipopolysaccharide activates Akt in human alveolar macrophages resulting in nuclear accumulation and transcriptional activity of beta-catenin, J Immunol. (2001) 166(7): 4713-4720.

Moore et al., Erlotinib plus Gemcitabine compared with Gemcitabine alone in patients with advanced pancreatic cancer: A phase III trial of the National Cancer Institute of Canada Clinical Trials Group. J Clin Oncol. (2007); 25(15): 1960-1966.

Mori et al., CXCR4 antagonist inhibits stromal cell-derived factor 1-induced migration and invasion of human pancreatic cancer, Mol Cancer Ther. (2004) 3(1): 29-37.

Murakami et al., The novel CXCR4 antagonist KRH-3955 is an orally bioavailable and extremely potent inhibitor of human immunodeficiency virus type 1 infection: comparative studies with AMD3100, Antimicrob Agents and Chemother. (2009) 53(7): 2940-2948.

Olive et al., Inhibition of Hedgehog signaling enhances delivery of chemotherapy in a mouse model of pancreatic cancer, Science (2009) 324(5933): 1457-1461.

Ozes et al., NF-kappaB activation by tumour necrosis factor requires the Akt serine-threonine kinase, Nature (1999) 401(6748): 82-85.

Paddison et al. Short hairpin RNAs (shRNAs) induce sequence-specific silencing in mammalian cells, Genes Dev. (2002) 16: 948-958.

Pardridge W. M., Intravenous, non-viral RNAi gene therapy of brain cancer, Expert Opin Biol Ther. (2004) 4(7): 1103-1113.

Paul et al., Effective expression of small interfering RNA in human cells, Nat Biotechnol. (2002) 20: 505-508.

Pei et al., FKBP51 affects cancer cell response to chemotherapy by negatively regulating Akt, Cancer Cell (2009) 16(3): 259-266.

Pelus et al., The CXCR4 agonist peptide, CTCE-0021, rapidly mobilizes polymorphonueclear neutrophils and hematopoietic progenitor cells into peripheral blood and synergizes with granulocyte colony-stimulated factor, Exp Hematol. (2005) 33(3): 295-307.

Réjiba et al., Gemcitabine-based chemogene therapy for pancreatic cancer using Ad-dCK::UMK GDEPT and TS/RR siRNA strategies, Neoplasia (2009) 11(7): 637-650.

Romashkova et al., NF-kappaB is a target of AKT in anti-apoptotic PDGF signaling. Nature (1999) 401(6748): 86-90.

Ryther et al., siRNA Therapeutics: big potential from small RNAs, Gene Ther. (2005) 12: 5-11.

(56) References Cited

OTHER PUBLICATIONS

Saur et al., CXCR4 expression increases liver and lung metastasis in a mouse model of pancreatic cancer. Gastroenter. (2005) 129: 1237-1250.

Scheid et al., Dissociation of cytokine-induced phosphorylation of Bad and activation of PKB/akt: involvement of MEK upstream of Bad phosphorylation, Proc Natl Acad Sci USA (1998) 95(13): 7439-7444.

Seufferlein et al., Tumor biology and cancer therapy—an evolving relationship. Cell Comm Signal. (2009); 5: 19; 10 pages.

Shah et al., Development and characterization of gemcitabine-resistant pancreatic tumor cells. Ann Surg Oncol. (2007) 14(1 2): 3629-3637.

Sharp P.A., RNA interference, Genes Dev. (2001) 15:485-490 by Cold Spring Harbor Laboratory Press.

Shen W.-G. RNA Interference and its current application in mammals, Chin. Med. J. (Engl) (2004) 117(7): 1084-1091.

Shen et al., Chemokine receptor CXCR4 enhances proliferation in pancreatic cancer cells through AKT and ERK dependent pathways. Pancreas (2010) 39(1): 81-87.

Sheridan et al., Oncogenic B-Raf$^{V600E}$ inhibits apoptosis and promotes ERK-dependent inactivation of Bad and Bim,. J Bioli Chem. (2008) 283(32): 22128-22135.

Singh et al., Inhibition of *MUC4* expression suppresses pancreatic tumor cell growth and metastasis. Cancer Res. (2004) 64(2): 622-630.

Singh et al., Chemokines in tumor angiogenesis and metastasis, Cancer Metastasis Rev, (2007) 26(3-4): 453-467.

Singh et al., CXCL12-CXCR4 signaling axis confers gemcitabine resistance to pancreatic cancer cells: a novel target for therapy, Br J Cancer. (Nov. 2010); 103(11): 1671-1679.

Sizemore et al., Activation of phosphatidylinositol 3-kinase in response to interleukin-1 leads to phosphorylation and activation of the NF-kappaB p65/RelA subunit, Mol Cell Biol. (1999) 19(7): 4798-4805.

Sui et al., A DNA vector-based RNAi technology to suppress gene expression in mammalian cells, Proc. Natl. Acad. Sci. USA. (2002) 99(6):5515-5520.

Takaku H., Gene silencing of HIV-1 by RNA interference, Antivir Chem Chemother (2004) 15: 57-65.

Tamamura et al., Identification of a CXCR4 antagonist, a T140 analog, as an anti-rheumatoid arthritis agent, FEBS Lett. (2004) 569(1-3): 99-104.

Taxman et al., Criteria for effective design, construction, and gene knockdown by shRNA vectors, BMC Biotechnol. (2006) 6: 7; 16 pages.

Tchernychev et al., Discovery of a CXCR4 agonist pepducin that mobilizes bone marrow hemotopoietic cells, Proc Natl Acad Sci U S A. (2010) 107(51): 22255-22259.

Thomas et al., The chemokine receptor CXCR4 is expressed in pancreatic intraepithelial neoplasia, Gut (2008) 57(11): 1555-1560.

Tudan et al., C-terminal cyclization of an SDF-1 small peptide analogue dramatically increases receptor affinity and activation of the CXCR4 receptor, J Med Chem. (2002) 45(10): 2024-2031.

Tuschl, T. Expanding small RNA interference, Nat Biotechnol. (2002) 20: 446-448.

Wadhwa et al. Know-how of RNA interference and its applications in research and therapy, Mutat Res. (2004) 567: 71-84.

Wang et al., Acquisition of epithelial-mesenchymal transition phenotype of gemcitabineresistant pancreatic cancer cells is linked with activation of the notch signaling pathway, Cancer Res (2009) 69(6): 2400-2407.

Wang et al., Dihydroartemisinin inactivates NF-kappaB and potentiates the anti-tumor effect of gemcitabine on pancreatic cancer both in vitro and in vivo, Cancer Lett. (2010) 293(1): 99-108.

Wong et al., Pancreatic cancer: molecular pathogenesis and new therapeutic targets. Nat Rev Gastroenterol Hepatol. (2009) 6(7): 412-422.

Yasumoto et al., Role of the CXCL12/CXCR4 axis in peritoneal carcinomatosis of gastric cancer, Cancer Res. (2006) 66(4): 2181-2187.

Yokoi et al., Hypoxia increases resistance of human pancreatic cancer cells to apoptosis induced by gemcitabine. Clin Cancer Res. (2004) 10(7): 2299-2306.

Yu et al., RNA Interference by expression of short-interfering RNAs and hairpin RNAs in mammalian cells, Proc. Natl. Acad. Sci. USA. (2002) 99(9): 6047-6052.

Zhao et al., Mitogen-activated protein kinases and chemoresistance in pancreatic cancer cells. J Surg Res. (2006) 136(2): 325-335.

Zheng et al., Prophylactic and therapeutic effects of small interfering RNA targeting SARS-coronavirus, Antivir Ther. (2004) 9: 365-374.

International Search Report and Written Opinion dated May 9, 2012 for Application No. PCT/US2011/057751.

\* cited by examiner

METHODS AND COMPOSITIONS FOR AMELIORATING PANCREATIC CANCER

REFERENCE TO RELATED APPLICATIONS

This application is a continuation of Ser. No. 13/881,695 filed Apr. 25, 2013 entitled "METHODS AND COMPOSITIONS FOR AMELIORATING PANCREATIC CANCER" which is the U.S. National Phase of Application No. PCT/US2011/057751 entitled "METHODS AND COMPOSITIONS FOR AMELIORATING PANCREATIC CANCER" filed Oct. 25, 2011 and published in English on May 3, 2012 as WO2012/058241 which claims the benefit of U.S. Provisional Application No. 61/455,795 entitled "TARGETING CXCL12-CXCR4 SIGNALING AXIS TO OVERCOME GEMCITABINE-RESISTANCE TO PANCREATIC CANCER CELLS" and filed Oct. 26, 2010, the disclosure of which is incorporated herein by reference in its entirety.

STATEMENT REGARDING FEDERALLY SPONSORED R&D

This work is supported, in part, by a grant from the National Institutes of Health (CA137513). The government may have rights in the subject matter provided herein.

REFERENCE TO SEQUENCE LISTING

The present application is being filed along with a Sequence Listing in electronic format. The Sequence Listing is provided as a file entitled USA011C1TXT, created Jan. 26, 2016, which is approximately 17 KB in size. The information in the electronic format of the Sequence Listing is incorporated herein by reference in its entirety.

FIELD OF THE INVENTION

Embodiments of the present invention include methods and compositions for ameliorating cancer. Some embodiments include methods and compositions for ameliorating pancreatic cancer targeting the CXCR4 receptor and the CXCL12 ligand.

BACKGROUND OF THE INVENTION

Pancreatic cancer is a highly lethal malignancy with an extremely poor prognosis. The overall median survival after diagnosis is 2-8 months, and only 1-4% of all patients with pancreatic adenocarcinoma survive 5 years after diagnosis (Singh et al., 2004). According to an estimate of the American Cancer Society, 42,470 Americans were diagnosed with pancreatic cancer in 2009 and 35,240 died from it, marking this malignancy as the fourth leading cause of cancer deaths (Jemal et al., 2009). Surgical resection is the best and most effective choice for treatment, but in majority of cases, the disease is locally advanced or has already metastasized to distant organs at the time of diagnosis. In the latter scenario, chemotherapy is considered as an option, but the effects are usually modest due to chemo-resistance (Rejiba et al., 2009; Liau and Whang, 2008). Drug-resistance in pancreatic cancer cells is thought to occur mainly as a result of active survival mechanisms and/or inefficient drug delivery because of the fibrotic nature of pancreatic tumors (Olive et al., 2009; Pei et al., 2009). Hence, there is an urgent need to develop alternative strategies and novel therapeutics for effective treatments of this devastating malignancy and improve clinical outcome.

SUMMARY OF THE INVENTION

Embodiments of the present invention include methods and compositions for ameliorating cancer. Some embodiments include methods and compositions for ameliorating pancreatic cancer targeting the CXCR4 receptor and the CXCL12 ligand. Some embodiments provided herein relate to methods of reducing the resistance of a tumor cell to a chemotherapeutic agent comprising inhibiting CXCL12. In some embodiments, inhibiting CXCL12 comprises contacting the cell with a CXCR4 antagonist.

In some embodiments, the CXCR4 antagonist is selected from the group consisting of Plerixafor (AMD3100), BKT140, TN14003, CTCE-9908, KRH-2731, TC14012, KRH-3955, and AMD070. In some embodiments, the CXCR4 antagonist comprises Plerixafor (AMD3100).

In some embodiments, inhibiting CXCL12 comprises reducing expression of a nucleic acid encoding CXCR4.

In some embodiments, reducing the expression of a nucleic acid encoding CXCR4 comprises contacting the cell with a nucleic acid selected from the group consisting of an antisense RNA, siRNA and ribozyme.

In some embodiments, the tumor cell comprises a pancreatic tumor cell. In some embodiments, the tumor cell is selected from the group consisting of CFPAC-1, AsPc-1, SW1990, Colo-357, MiaPaCa, Panc1, Panc02.37, Panc10.05, BxPC3, Panc02.03, HPAF-II, and CaPan-1.

In some embodiments, the tumor cell comprises a mammalian tumor cell. In some embodiments, the tumor cell comprises a human tumor cell.

In some embodiments, the chemotherapeutic agent comprises gemcitabine. In some embodiments, the chemotherapeutic agent comprises gemcitabine and erlotinib.

Some embodiments provided herein relate to methods of reducing growth of a tumor cell comprising inhibiting CXCL12.

In some embodiments, inhibiting CXCL12 comprises contacting the tumor cell with a CXCR4 antagonist. In some embodiments, the CXCR4 antagonist is selected from the group consisting of Plerixafor (AMD3100), BKT140, TN14003, CTCE-9908, KRH-2731, TC14012, KRH-3955, and AMD070. In some embodiments, the CXCR4 antagonist comprises Plerixafor (AMD3100).

In some embodiments, inhibiting CXCL12 comprises reducing the expression of a nucleic acid encoding CXCR4.

In some embodiments, reducing the expression of a nucleic acid encoding CXCR4 comprises contacting the tumor cell with a nucleic acid selected from the group consisting of an antisense RNA, siRNA and ribozyme.

In some embodiments, the tumor cell comprises a pancreatic tumor cell. In some embodiments, the tumor cell is selected from the group consisting of CFPAC-1, AsPc-1, SW1990, Colo-357, MiaPaCa, Panc1, Panc02.37, Panc10.05, BxPC3, Panc02.03, HPAF-II, and CaPan-1.

In some embodiments, the tumor cell comprises a mammalian tumor cell. In some embodiments, the tumor cell comprises a human tumor cell.

Some embodiments provided herein relate to methods of enhancing apoptosis in a tumor cell comprising inhibiting CXCL12.

In some embodiments, inhibiting CXCL12 comprises contacting the tumor cell with a CXCR4 antagonist. In some embodiments, the CXCR4 antagonist is selected from the group consisting of Plerixafor (AMD3100), BKT140, TN14003, CTCE-9908, KRH-2731, TC14012, KRH-3955, and AMD070. In some embodiments, the CXCR4 antagonist comprises Plerixafor (AMD3100).

In some embodiments, inhibiting CXCL12 comprises reducing the expression of a nucleic acid encoding CXCR4.

In some embodiments, reducing the expression of a nucleic acid encoding CXCR4 comprises contacting the tumor cell with a nucleic acid selected from the group consisting of an antisense RNA, siRNA and ribozyme.

In some embodiments, the tumor cell comprises a pancreatic tumor cell. In some embodiments, the tumor cell is selected from the group consisting of CFPAC-1, AsPc-1, SW1990, Colo-357, MiaPaCa, Panc1, Panc02.37, Panc10.05, BxPC3, Panc02.03, HPAF-II, and CaPan-1.

In some embodiments, the tumor cell comprises a mammalian tumor cell. In some embodiments, the tumor cell comprises a human tumor cell.

Some embodiments provided herein relate to methods of identifying a therapeutic compound comprising contacting a target cell with a test compound and a CXCR4 agonist; and determining whether the test compound significantly changes the level of expression or activity in the target cell of a protein selected from the group consisting of FAK, Akt, ERK, β-catenin, NF-κB, Bcl-2, Bcl-xL, Notch1, phosphorylated BAD, and SHH.

In some embodiments, the CXCR4 agonist comprises CXCL12.

Some embodiments also include comparing the level of the protein in a target cell which has been contacted with the CXCR4 agonist and has not been contacted with the test compound to the level of the protein in a target cell contacted with the test compound and the CXCR4 agonist.

Some embodiments also include determining whether the test compound decreases the level or activity of the protein.

In some embodiments, the cell comprises a pancreatic cell. In some embodiments, the cell is selected from the group consisting of CFPAC-1, AsPc-1, SW1990, Colo-357, MiaPaCa, Panc1, Panc02.37, Panc10.05, BxPC3, Panc02.03, HPAF-II, and CaPan-1.

In some embodiments, the cell comprises a tumor cell.

In some embodiments, the cell comprises a mammalian cell. In some embodiments, the cell comprises a human cell.

Some embodiments provided herein relate to methods of ameliorating cancer in a subject comprising administering an effective amount of a CXCL12 inhibitor to the subject.

In some embodiments, the CXCL12 inhibitor comprises a CXCR4 antagonist. In some embodiments, the CXCR4 antagonist is selected from the group consisting of Plerixafor (AMD3100), BKT140, TN14003, CTCE-9908, KRH-2731, TC14012, KRH-3955, and AMD070. In some embodiments, the CXCR4 antagonist comprises Plerixafor (AMD3100).

Some embodiments also include administering a chemotherapeutic agent to the subject.

In some embodiments, the administration of the CXCL12 inhibitor to the subject decreases the resistance of the tumor to the chemotherapeutic agent.

In some embodiments, the cancer comprises pancreatic cancer.

In some embodiments, the subject is mammalian. In some embodiments, the subject is human.

Some embodiments provided herein relate to kits for identifying a therapeutic agent comprising a CXCL12 inhibitor; and an isolated tumor cell.

In some embodiments, the CXCL12 inhibitor comprises a CXCR4 antagonist. In some embodiments, the CXCR4 antagonist is selected from the group consisting of Plerixafor (AMD3100), BKT140, TN14003, CTCE-9908, KRH-2731, TC14012, KRH-3955, and AMD070. In some embodiments, the CXCR4 antagonist comprises Plerixafor (AMD3100).

In some embodiments, the cell comprises a pancreatic cell. In some embodiments, the cell is selected from the group consisting of CFPAC-1, AsPc-1, SW1990, Colo-357, MiaPaCa, Panc1, Panc02.37, Panc10.05, BxPC3, Panc02.03, HPAF-II, and CaPan-1.

In some embodiments, the cell comprises a mammalian cell. In some embodiments, the cell comprises a human cell.

BRIEF DESCRIPTION OF THE DRAWINGS

FIG. 1 (panel A) depicts a Western blot. Total protein was isolated from twelve pancreatic cancer cell lines and resolved on 10% SDS polyacrylamide gels by electrophoresis; the gels were immunoblotted with anti-CXCR4 rabbit polyclonal antibodies and reprobed with anti-β actin (internal control) mouse monoclonal antibody. CXCR4 was expressed at varying levels in all pancreatic cancer cell lines tested. FIG. 1 (panel B) depicts a graph of CXCL12 expression in various pancreatic cancer cell lines. An enzyme-linked immunosorbant assay (ELISA) was performed on conditioned culture media from pancreatic cancer cells grown under serum-free conditions for 72 h using a commercial kit. Low level of CXCL12 expression (13-230 pg/mL/$10^6$ cells) was detected in all pancreatic cancer cell lines. FIG. 1 (panel C) depicts a graph of relative growth of MiaPaCa and Panc1 pancreatic cancer cells upon CXCL12 treatment (100 ng/ml) indicating the functionality of CXCL12-CXCR4 signaling axis. CXCL12 stimulation (in serum-deprived and -supplemented media) led to the significant induction (*$p<0.01$) of growth in pancreatic cancer cells. Responses were more pronounced under serum-free conditions than in serum-containing cultures likely due to the compensatory growth promoting effects of other serum factors.

FIG. 2A and FIG. 2B depict graphs of relative survival of the pancreatic cancer cells, Panc1 and MiaPaCa, respectively. Cells were treated with various doses of gemcitabine (0-10 μM) under serum-supplemented condition in presence and absence of CXCL12 (100 ng/mL). Cancer cell viability was examined 72 h post-treatment by MTT assay. Significant protection of pancreatic cancer cells from gemcitabine toxicity (at 5 and 10 μM) by CXCL12 was observed. Data is presented as relative survival with respect to untreated or CXCL12 only-treated cells to control for the growth promoting effect of CXCL12 (*$p<0.01$).

FIG. 3 (panel A) depicts a photomicrograph of a DNA fragmentation assay. Cells were seeded in 6 cm Petri-dishes and treated with 5 and 10 μM gemcitabine in the absence or presence of CXCL12 (100 ng/mL) for 48 h. Subsequently, genomic DNA was isolated and resolved (2 μg/lane) on 1% agarose gel. Lane 1: untreated, lanes 2 & 3: gemcitabine-treated (5 and 10 μM), respectively, and lanes 4 & 5: gemcitabine-treated (5 and 10 μM, respectively) in presence of CXCL12. CXCL12-treated pancreatic cancer cells exhibit reduced DNA laddering compared to cells treated with gemcitabine only. FIG. 3 (panel B) relates to an in situ determination of apoptosis, and depicts a series of photomicrographs of treated cells. Panc1 and MiaPaCa cells were cultured on chamber slides and treated with gemcitabine (5 μM) in absence and presence of CXCL12 (100 ng/mL).

Apoptosis was detected by staining the cells with CaspACE FITC-VAD-FMK solution in PBS for 2 h at 37° C. Following fixation, bound marker was visualized by fluorescent detection under a confocal microscope. CXCL12 co-treated cells exhibit reduced apoptosis by gemcitabine as evident by the decreased fluorescence intensity and number of positively (dark green florescent) stained cells. Representative pictures are from one of the random fields of untreated (upper panel), gemcitabine only (middle panel) and gemcitabine+CXCL12-treated (lower panel) MiaPaCa cells. Similar findings were also reported for Panc1 cells (data not shown). DAPI stained cells: subpanels a, d, and g; FITC stained cells: panels b, e, and h: Overlay: subpanels c, f, and i.

Figure 4:
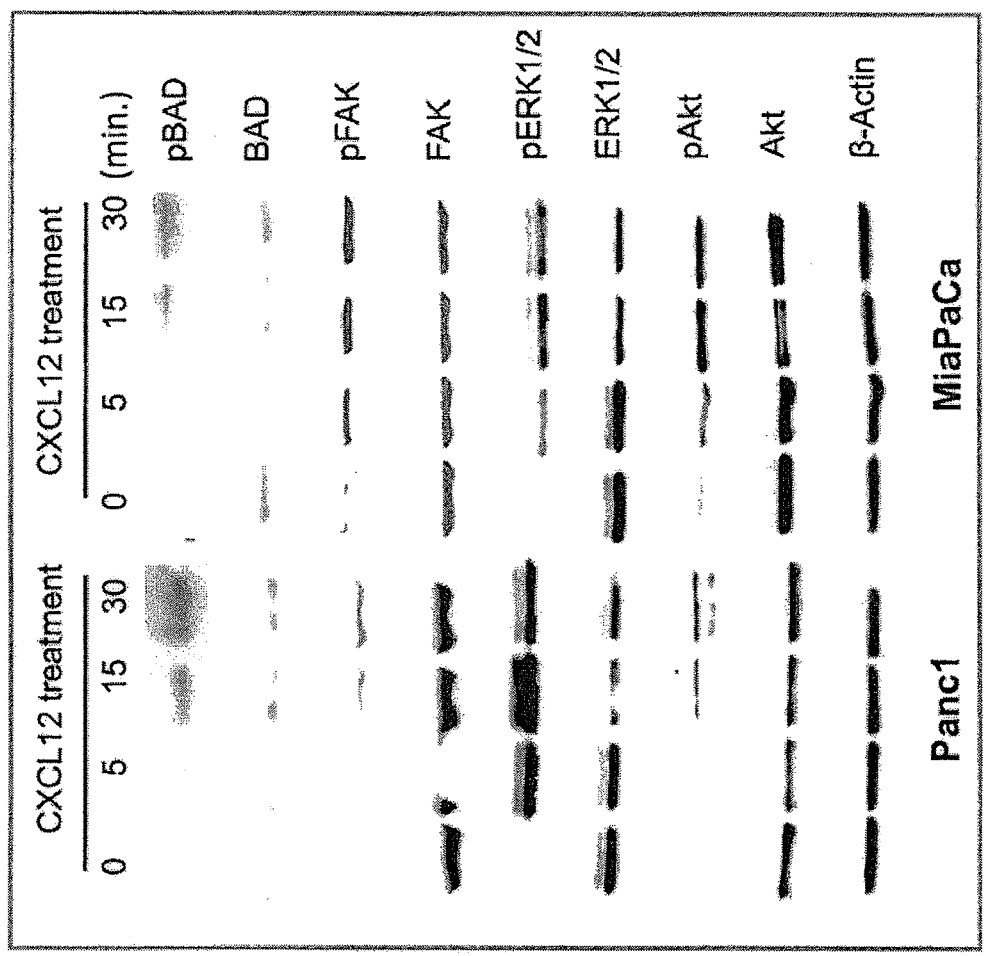

FIG. 4 relates to CXCL12-induced activation of FAK, Akt and ERK pathways and depicts Western blots. Sub-confluent Panc1 and MiaPaCa cell cultures were treated with CXCL12 (100 ng/mL) for 5, 15 and 30 min durations. Protein was extracted and resolved on SDS-polyacrylamide gels by electrophoresis. Activation of FAK, Akt and ERK pathways was assessed by immunoblotting using total and phospho-form specific antibodies as indicated. B-Actin served as an internal control. CXCL12-treatment induced the phosphorylation of all three effector proteins with a concomitant inactivating phosphorylation of pro-apoptotic BAD protein in both Panc1 and MiaPaCa cell lines.

Figure 5:
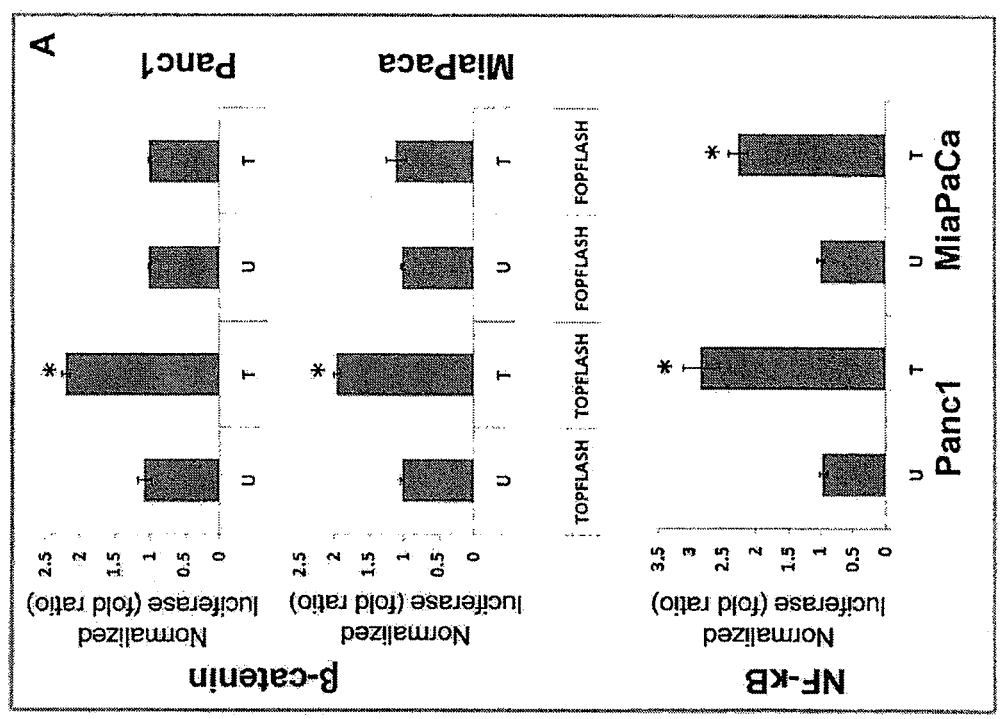
Figure 5:
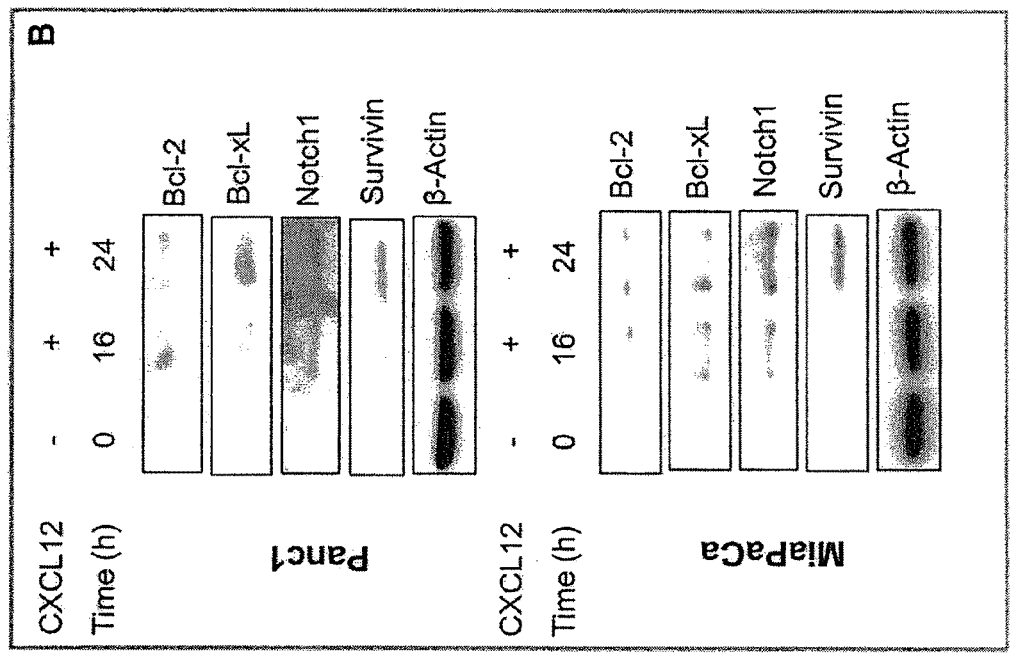

FIG. 5 (panels A and B) relates to induction of β-catenin/TCF and NF-κB transcriptional activities and expression of survival proteins by CXCL12 in pancreatic cancer cells. FIG. 5 (panel A) depicts graphs for relative β-catenin and NF-κB activity in Panc1 and MiaPaCa cells. Pancreatic cancer cells were transfected with TOPflash or FOPflash or NF-κB luciferase reporter constructs along with *Renilla luciferase* construct to control for the transfection efficiency. Cells were treated with CXCL12 24 h post-transfection and protein isolated in passive lysis buffer. Luciferase activity was assessed using a dual-luciferase assay system and data presented as fold change in luciferase activity after normalization. Bars represent the average of triplicates+S.D., *, statistically significant difference (p<0.01). FIG. 5 (panel B) depicts Western blots showing the change in expression of Bcl-2, Bcl-xL, Notch I and survivin examined in CXCL12-treated cells at different time durations by immunoblotting. An increased expression of all the four survival proteins was detected in CXCL12-treated pancreatic cancer cells.

Figure 6:
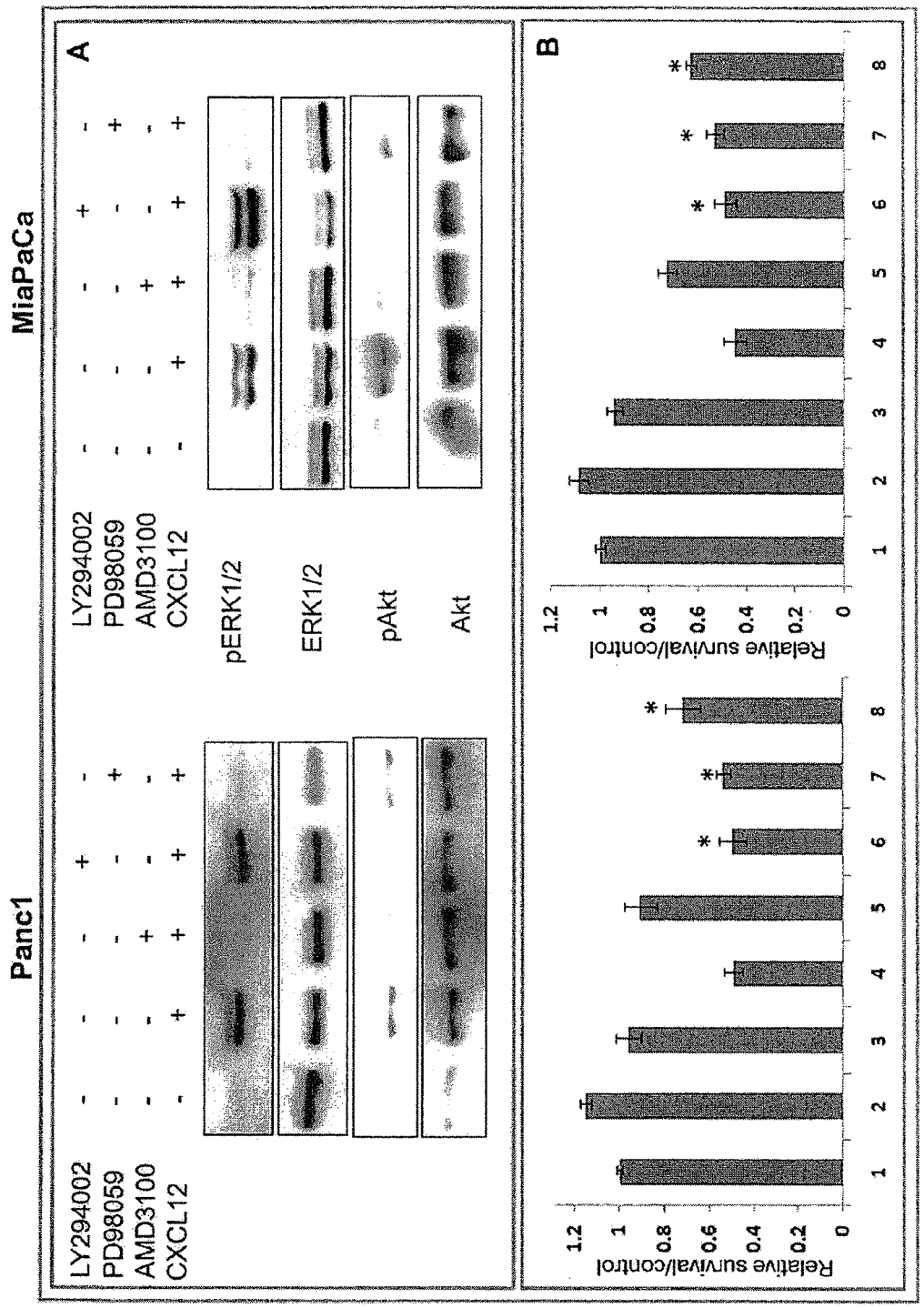

FIG. 6 (panels A and B) relates to the effect of CXCR4 targeting and blockade of PI3K or Erk pathways on the cytoprotective effect of CXCL12 in pancreatic cancer cells from gemcitabine-induced toxicity. FIG. 6 (panel A) depicts Western blots of pancreatic cancer cells (Panc1 and MiaPaCa) treated with AMD31 00 (5 g/mL) or LY294002 (20 μM) or PD98059 (25 μM) for 1 h prior to induction with CXCL12. Total protein was isolated 15 min post-CXCL12 treatment and activation of Akt and ERK was examined by immunoblotting for their total and phospho-forms. AMD3100 inhibited the activation of both Akt and ERK pathways, while LY294002 and PD980S9 specifically inhibited Akt and ERK pathways, respectively. FIG. 6 (panel B) depicts graphs of relative survival of cells. Cells were pre-treated with AMD3100 or LY294002 or PD980S9 or PBS for 1 h. Subsequently, cells were treated with CXCL12 or gemcitabine either alone or in combination. Cell viability was assessed by MIT assay. Bars represent the average of triplicates±S.D.; *, statistically significant difference (p<0.01) with respect to Gemcitabine+CXCL12-treated cells. Bars 1: untreated, 2: CXCL12-treated, 3: AMD3100-pretreated+CXCL12-treated, 4: gemcitabine-treated, 5: gemcitabine+CXCL12-treated, 6: AMD3100-pretreated+gemcitabine+CXCL12-treated, 7: LY294002-pretreated+gemcitabine+CXCL12-treated, and 8: PD980S9-pretreated+gemcitabine+CXCL12-treated.

Figure 7:
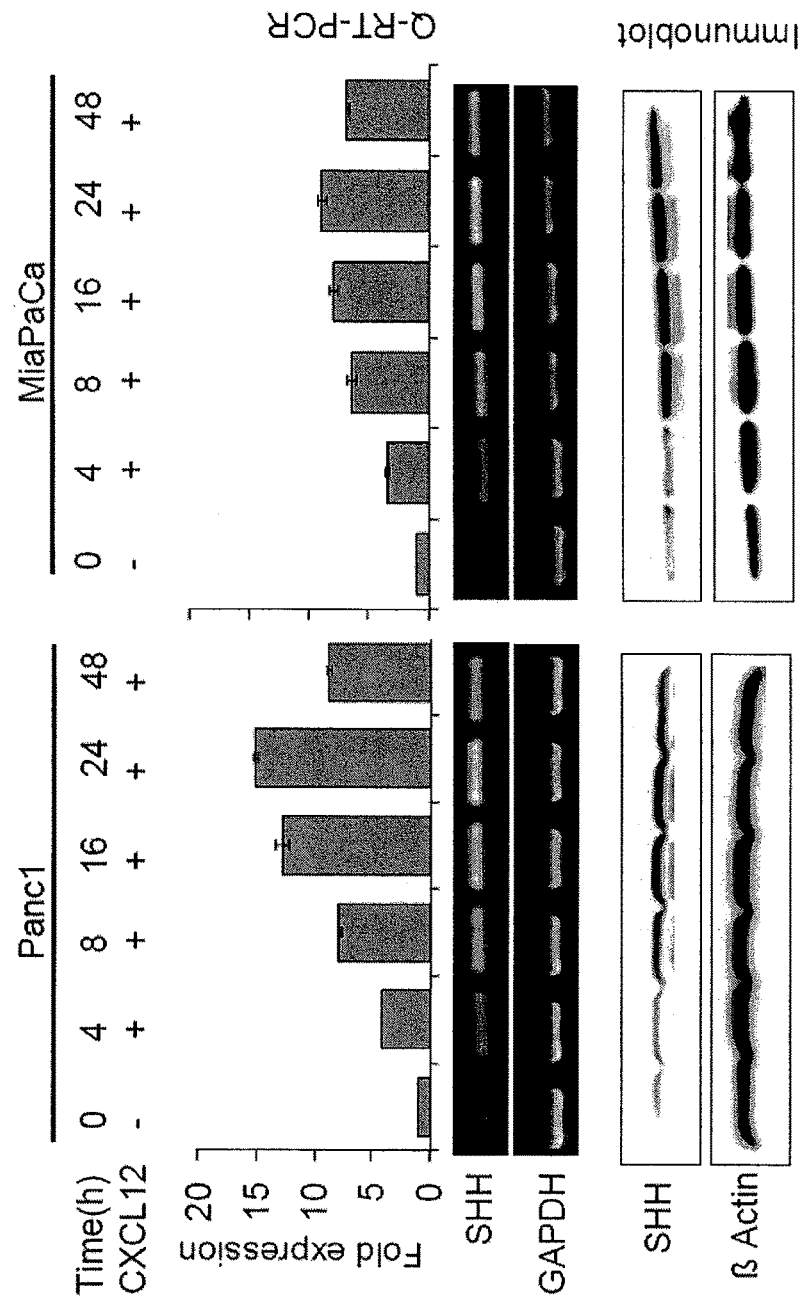

FIG. 7 relates to a time-course of CXCL12-induced sonic hedgehog (SHH) expression in Panc1 (left-most six columns/lanes) and MiaPaCa (right-most six columns/lanes) treated cells, and depict graphs of fold-expression of sonic hedgehog (SHH) measured using Q-RT-PCR, and photomicrographs of agarose gels of amplified products and Western blots of protein expression of SHH.

DETAILED DESCRIPTION

Embodiments of the present invention relate to methods and compositions for ameliorating cancer. Some embodiments include methods and compositions for ameliorating pancreatic cancer targeting the CXCR4 receptor and the CXCL12 ligand. Pancreatic cancer cells are highly resistant to drug therapy; however, underlying causes remain largely unknown. Activation of CXCL12-CXCR4 signaling may confer drug-resistance to pancreatic cancer cells by potentiating survival. CXCR4 is overexpressed in precancerous/malignant pancreatic lesions and cancer stem cells, and implicated in its pathogenesis. As described in this application, pancreatic cancer cells treated with gemcitabine exhibited reduced cytotoxicity in presence of CXCL12 as compared to the cells treated with drug alone. CXCL12 induced the activation of FAK, ERK and Akt signaling pathways, enhanced transcriptional activities of β-catenin and NF-κB, and expression of survival proteins. AMD3100 arrested the CXCL12-induced pancreatic cancer cell growth and drug-resistance. These findings demonstrate a role of the CXCL12/CXCR4 signaling axis in conferring drug-resistance to pancreatic cancer cells and suggest a novel therapeutic target for pancreatic cancer therapy.

The chemokine receptor, CXCR4, is expressed in a variety of malignancies and has been extensively studied for its role in cancer pathogenesis (Singh et al., 2007; Gelmini et al., 2008). CXCR4 expression is elevated in majority of pancreatic cancer tissues and pre-cancerous lesions, suggesting its role in pancreatic cancer pathogenesis (Marechal et al., 2009; Thomas et al., 2008). CXCL12, a ligand for CXCR4, is also abundantly produced by neighboring stromal cells and activation of CXCR4-expressing pancreatic cancer cells by CXCL12 leads to enhanced chemotaxis, transendothelial migration and Matrigel invasion (Matsuo et al., 2009; Marchesi et al., 2004). Furthermore, high concentrations of CXCL12 are present at the common sites of pancreatic metastases (lymph nodes, liver, lungs, etc.), suggesting that CXCL12-CXCR4 signaling may play a role in the homing of pancreatic cancer cells to specific organs (Saur et al., 2005; Mori et al., 2004). Importantly, a recent study also showed that a distinct subpopulation of $CD133^+$; $CXCR4^+$ cancer stem cells (CSCs) was present at the leading edge of invasive pancreatic tumors indicating a potential role of CXCR4 in the invasion process (Hermann et al., 2007). CXCR4 expressed on pancreatic cancer stem cells was shown to be essential for their invasive and metastatic properties, suggesting a strong correlation with disease aggression (Hermann et al., 2007). The CXCL12-CXCR4 signaling axis has also been implicated in desmoplastic alterations of surrounding stroma favoring tumor cell growth (Marlow et al., 2008). In other studies, CXCL12-CXCR4 signaling was shown to stimulate pancreatic cancer cell proliferation and protection of cancer cells from serum deprivation-induced apoptosis (Marchesi et al., 2004; Saur et al., 2005; Koshiba et al., 2000; Marlow et al., 2008). Altogether, these observations indicate an important role of CXCR4 signaling in pancreatic cancer survival, proliferation, invasion, and metastasis, suggesting this signaling axis as a potential target for cancer therapy.

Gemcitabine is the only FDA-approved chemotherapeutic drug for the treatment of advanced and metastatic pancreatic cancer. However, it has not proven very effective clinically and improvement in patient's survival undergoing gemcitabine therapy is only minimal (Olive et al., 2009; Wong and Lemoine, 2009). It was hypothesized that the CXCL12-CXCR4 signaling axis is involved in pancreatic cancer drug-resistance by stimulating intrinsic cell survival mechanisms. The effect of CXCL12 in restricting the gemcitabine-induced toxicity of pancreatic cancer cells and activation of survival signaling pathways was investigated. Furthermore, the therapeutic significance of a CXCR4 antagonist, AMD3100, in preventing the rescue effect of activated CXCL12-CXCR4 signaling was examined. The data demonstrated that CXCL12 induces a series of signaling events in pancreatic cancer cells and counteracts the cytotoxic effects of gemcitabine. In addition, the data shows that AMD3100 can abrogate the survival effect of CXCL12-CXCR4 signaling and can serve as a therapeutic modality either alone or in combination with Gemcitabine to effectively inhibit the growth of pancreatic cancer cells.

Methods of Treatment

Some embodiments provided herein relate to methods for reducing the resistance of a tumor cell to chemotherapy. More embodiments provided herein relate to increasing the sensitivity of a tumor cell to a chemotherapeutic compound. More embodiments provided herein relate to methods for reducing growth of a tumor cell. More embodiments provided herein relate to methods of ameliorating cancer in a subject.

In some embodiments, the tumor cell comprises a mammalian cell. In some embodiments, the tumor cell comprises a human cell. In some embodiments, the tumor cell comprises a pancreatic cell. In some embodiments, the tumor cell comprises a cell selected from a pancreatic tumor cell line, such as CFPAC-1, AsPc-1, SW1990, Colo-357, MiaPaCa, Panc1, Panc02.37, Panc10.05, BxPC3, Panc02.03, HPAF-II, and CaPan-1.

Some of the foregoing methods can include inhibiting CXCL12, such as contacting a cell with a CXCL12 inhibitor. In some embodiments, inhibiting CXCL12 can include contacting a tumor cell with an effective amount of a CXCR4 antagonist. In some embodiments, the tumor cell is contacted with the CXCR4 antagonist in vitro. In some embodiments, the tumor cell is contacted with the CXCR4 antagonist ex vivo or in vivo. Examples of CXCR4 antagonists Plerixafor (AMD3100), BKT140, TN14003, CTCE-9908, KRH-2731, TC14012, KRH-3955, and AMD070. In particular embodiments, the antagonist comprises Plerixafor (AMD3100).

In some embodiments, inhibiting CXCL12 can include reducing the level of expression of a nucleic acid encoding CXCR4. Methods to reduce the level of expression of a nucleic acid in a cell are well known in the art some of which are described herein, such as RNA interference or antisense technologies. Examples of methods for reducing the level of expression of a nucleic acid in a cell include contacting a cell with an effective amount of a nucleic acid such as an antisense RNA, a siRNA, or a ribozyme. In some embodiments, the tumor cell is contacted with the CXCL12 inhibitor in vitro. In some embodiments, the tumor cell is contacted with the CXCL12 inhibitor in vivo.

In some embodiments, increasing the sensitivity of a tumor cell to a chemotherapeutic compound can include contacting the cell with an effective amount of a CXCL12 inhibitor and an effective amount of a chemotherapeutic agent. In some embodiments, the effective amount of the chemotherapeutic compound is less than the effective amount of the chemotherapeutic compound in the absence of the CXCL12 inhibitor by at least about 10%, 20%, 30%, 40%, 50%, 60%, 70%, 80%, 90%, 100%, or more. In some embodiments, the effective amount of the CXCL12 inhibitor is an amount which significantly reduces the IC50 of the chemotherapeutic compound. In some such embodiments, the IC50 of the chemotherapeutic agent is reduced by at least about 10%, 20%, 30%, 40%, 50%, 60%, 70%, 80%, 90%, 100%, or more.

In some embodiments, decreasing the resistance of a tumor cell to a chemotherapeutic compound can include contacting the cell with an effective amount of a CXCL12 inhibitor and an effective amount of a chemotherapeutic agent. In some embodiments, the effective amount of the chemotherapeutic compound is less than the effective amount of the chemotherapeutic compound in the absence of the CXCL12 inhibitor by at least about 10%, 20%, 30%, 40%, 50%, 60%, 70%, 80%, 90%, 100%, or more. In some embodiments, the effective amount of the CXCL12 inhibitor is an amount which significantly reduces the IC50 of the chemotherapeutic compound. In some such embodiments, the IC50 of the chemotherapeutic agent is reduced by at least about 10%, 20%, 30%, 40%, 50%, 60%, 70%, 80%, 90%, 100%, or more.

In some embodiments, increasing the cytotoxicity of a chemotherapeutic compound to a tumor cell can include contacting the cell with an effective amount of a CXCL12 inhibitor and an effective amount of a chemotherapeutic agent. In some embodiments, the effective amount of the chemotherapeutic compound is less than the effective amount of the chemotherapeutic compound in the absence of the CXCL12 inhibitor by at least about 10%, 20%, 30%, 40%, 50%, 60%, 70%, 80%, 90%, 100%, or more. In some embodiments, the effective amount of the CXCL12 inhibitor is an amount which significantly reduces the IC50 of the chemotherapeutic compound. In some such embodiments, the IC50 of the chemotherapeutic agent is reduced by at least about 10%, 20%, 30%, 40%, 50%, 60%, 70%, 80%, 90%, 100%, or more.

Contacting a cell with a CXCL12 inhibitor in combination with a chemotherapeutic agent can include contacting the cell with the CXCL12 inhibitor and the chemotherapeutic agent at the same time, at different times, and at overlapping time periods. The cell inhibitor may be contacted with the CXCL12 inhibitor before, after, or during the period of time the cell is contacted with the chemotherapeutic agent. In some embodiments, contacting the cell with the chemotherapeutic agent commences before contacting the cell with the CXCL12 inhibitor. In some embodiments, contacting the cell with the chemotherapeutic agent is before contacting the cell with the CXCL12 inhibitor. In some embodiments, contacting the cell with the CXCL12 inhibitor commences before contacting the cell with the chemotherapeutic agent. In some embodiments, contacting the cell with the CXCL12 inhibitor is before contacting the cell with the chemotherapeutic agent.

In some embodiments, the time period between contacting the cell with the chemotherapeutic agent and contacting the cell with the CXCL12 inhibitor is less than or more than about 5 minutes, 10 minutes, 20 minutes, 30 minutes, 40 minutes, 50 minutes, or 60 minutes. In some embodiments, the period of time between contacting the cell with the chemotherapeutic agent and contacting the cell with the CXCL12 inhibitor is less than or more than about 1 hour, 2 hours, 3 hours, 4 hours, 5 hours, 6 hours, 7 hours, 8 hours, 9 hours, 10 hours, 11 hours, or 12 hours. In some embodiments, the period of time between contacting the cell with the chemotherapeutic agent and contacting the cell with the CXCL12 inhibitor is less than or more than about 12 hour, 24 hours, 36 hours, or 48 hours.

Some embodiments include methods of ameliorating cancer in a subject. Some such embodiments include administering an effective amount a CXCL12 inhibitor and an effective amount of the chemotherapeutic compound to the subject, wherein the effective amount of the chemotherapeutic compound is significantly less than the effective amount of the chemotherapeutic compound in the absence of the CXCL12 inhibitor. Some embodiments include methods for reducing the dosage of a chemotherapeutic agent needed to treat a cancer in a subject. Some such embodiments include administering an effective amount a CXCL12 inhibitor and an effective amount of the chemotherapeutic compound to the subject, wherein the effective amount of the chemotherapeutic compound is significantly less than the effective amount of the chemotherapeutic compound in the absence of CXCL12 inhibitor. More embodiments include decreasing the resistance of a cancer in a subject to a chemotherapeutic compound. More embodiments include increasing the sensitivity of a cancer in a subject to a chemotherapeutic compound. Some such embodiments include administering an effective amount a CXCL12 inhibitor and an effective amount of the chemotherapeutic compound to the subject, wherein the effective amount of the chemotherapeutic compound is significantly less than the effective amount of the chemotherapeutic compound in the absence of the CXCL12 inhibitor. In particular embodiments, the cancer comprises a pancreatic cancer. In some embodiments, the chemotherapeutic compound comprises gemcitabine. In some embodiments the chemotherapeutic compound comprises gemcitabine and Erlotinib.

CXCL12 Inhibitors

In some embodiments a CXCL12 inhibitor comprises a CXCR4 antagonist. Examples of CXCR4 antagonists include:

Plerixafor (AMD3100; Mozobil), the structure of which is:

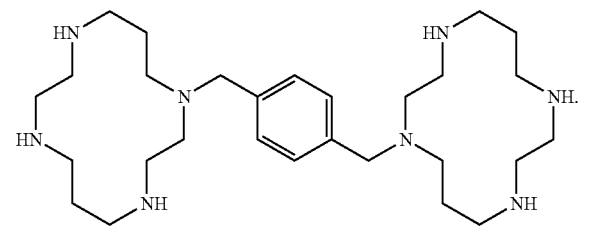 [SMILES: c1cc(CN2CCCNCCNCCCNCC2)ccc1CN1CCCNCCNCCCNCC1]

BKT140 (4F-benzoyl-TN14003; 4F-benzoyl-Arg-Arg-Nal-Cys-Tyr-Cit-Lys-DLys-Pro-Tyr-Arg-Cit-Cys-Arg-NH$_2$; (SEQ ID NO: 01) and those CXCR4 antagonists described in U.S. Pub. No. 20100184694, and U.S. Pat. No. 7,423,007, the contents of which are hereby incorporated by reference in their entireties.

TN14003 (H-Arg-Arg-Nal-Cys-Tyr-Cit-Lys-DLys-Pro-Tyr-Arg-Cit-Cys-Arg-OH, SEQ ID NO:06; Tamamura et al., 2004, FEBS Lett., 569:99; and Liang et al., 2004, Cancer Res., 64:4302, the contents of which are hereby incorporated by reference in their entireties).

CTCE-9908 (peptide antagonist of CXCR4 (amino acid sequence: KGVSLSYR-X-RYSLSVGK, SEQ ID NO:07; Chemokine Therapeutics Corp., Vancouver, Canada), and those CXCR4 antagonists described in WO 01/76615, WO 01/85196 and U.S. Pub. No. 20070160574, the contents of which are hereby incorporated by reference in their entireties.

KRH-2731 (CS-3955) and those CXCR4 antagonists described in WO2006/095542 and WO02/094261, the contents of which are hereby incorporated by reference in their entireties.

TC14012 (Arg-Arg-Nal-Cys-Tyr-Arg-Lys-DCit-Pro-Tyr-Arg-Cit-Cys-Arg-NH$_2$, (SEQ ID NO: 02), where Nal=L-3-(2-naphthylalanine), Cit=citruline and the peptide is cyclized with the cysteines) and those CXCR4 antagonists described in U.S. Pub. No. 20100184694 and U.S. Pub. No. 20100222256, the contents of which are hereby incorporated by reference in their entireties.

KRH-3955, the structure of which is:

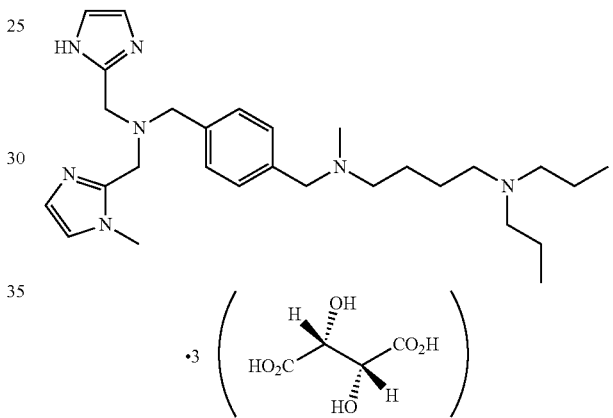

(Murakami T., et al., Antimicrobial Agents and Chemotherapy, 53:2940-2948, the contents of which is hereby incorporated by reference in its entirety).

AMD070 (also known as AMD11070), the structure of which is:

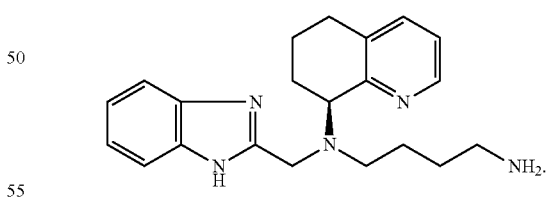

In addition to CXCR4 antagonists, some CXCL12 inhibitors include compounds that reduce the levels of CXCR4 protein or a nucleic acid encoding CXCR4 or CXCL12 protein or a nucleic acid encoding CXCl12. Examples of methods for reducing the levels of CXCR4 protein or a nucleic acid encoding CXCR4 or CXCL12 protein or a nucleic acid encoding CXCl12 include RNA interference or antisense technologies.

In some embodiments, the levels of CXCR4 protein or a nucleic acid encoding CXCR4 or CXCL12 protein or a nucleic acid encoding CXCl12 can be reduced using RNA interference or antisense technologies. RNA interference is an efficient process whereby double-stranded RNA (dsRNA), also referred to herein as siRNAs (small interfering RNAs) or ds siRNAs (double-stranded small interfering RNAs), induces the sequence-specific degradation of targeted mRNA in animal or plant cells (Hutvagner, G. et al. (2002) Curr. Opin. Genet. Dev. 12:225-232); Sharp, P. A. (2001) Genes Dev. 15:485-490, incorporated by reference herein in its entirety).

In mammalian cells, RNA interference can be triggered by various molecules, including 21-nucleotide duplexes of siRNA (Chiu, Y.-L. et al. (2002) Mol. Cell. 10:549-561. Clackson, T. et al. (1991) Nature 352:624-628.; Elbashir, S. M. et al. (2001) Nature 411:494-498), or by micro-RNAs (miRNA), functional small-hairpin RNA (shRNA), or other dsRNAs which can be expressed in vivo using DNA templates with RNA polymerase III promoters (Zheng, B. J. (2004) Antivir. Ther. 9:365-374; Paddison, P. J. et al. (2002) Genes Dev. 16:948-958; Lee, N. S. et al. (2002) Nature Biotechnol. 20:500-505; Paul, C. P. et al. (2002) Nature Biotechnol. 20:505-508; Tuschl, T. (2002) Nature Biotechnol. 20:446-448; Yu, J.-Y. et al. (2002) Proc. Natl. Acad. Sci. USA 99(9):6047-6052; McManus, M. T. et al. (2002) RNA 8:842-850; Sui, G. et al. (2002) Proc. Natl. Acad. Sci. USA 99(6):5515-5520, each of which are incorporated herein by reference in their entirety). The scientific literature is replete with reports of endogenous and exogenous gene expression silencing using siRNA, highlighting their therapeutic potential (Gupta, S. et al. (2004) PNAS 101:1927-1932; Takaku, H. (2004) Antivir Chem. Chemother 15:57-65; Pardridge, W. M. (2004) Expert Opin. Biol. Ther. 4(7):1103-1113; Shen, W.-G. (2004) Chin. Med. J. (Engl) 117:1084-1091; Fuchs, U. et al. (2004) Curr. Mol. Med. 4:507-517; Wadhwa, R. et al. (2004) Mutat. Res. 567:71-84; Ichim, T. E. et al. (2004) Am. J. Transplant 4:1227-1236; Jana, S. et al. (2004) Appl. Microbiol. Biotechnol. 65:649-657; Ryther, R. C. C. et al. (2005) Gene Ther. 12:5-11; Chae, S-S. et al. (2004) J. Clin. Invest 114:1082-1089; de Fougerolles, A. et al. (2005) Methods Enzymol. 392:278-296, each of which is incorporated herein by reference in its entirety). Some nucleic acid molecules or constructs provided herein include dsRNA molecules comprising 16-30, for example, 16, 17, 18, 19, 20, 21, 22, 23, 24, 25, 26, 27, 28, 29, or 30 nucleotides in each strand, wherein one of the strands is substantially identical, for example, at least 80% (or more, for example, 85%, 90%, 95%, or 100%) identical, for example, having 3, 2, 1, or 0 mismatched nucleotide(s), to a target region, such as in the mRNA of CXCR4 or CXCL12, and the other strand is identical or substantially identical to the first strand. An example method for designing dsRNA molecules is provided in the pSUPER RNAi SYSTEM™ (OligoEngine, Seattle, Wash.). More example methods are provided in Taxman D. J. et al. (2006) BMC Biotechnol. 6:7; and McIntyre G. J. et al. (2006) BMC Biotechnol. 6:1, each of which is incorporated by reference in its entirety.

Synthetic siRNAs can be delivered to cells by methods known in the art, including cationic liposome transfection and electroporation. siRNAs generally show short term persistence of the silencing effect (4 to 5 days in cultured cells), which may be beneficial in certain embodiments. To obtain longer term suppression of expression for targeted genes, such as CXCR4 or CXCL12, and to facilitate delivery under certain circumstances, one or more siRNA duplexes, for example, ds siRNA, can be expressed within cells from recombinant DNA constructs. Such methods for expressing siRNA duplexes within cells from recombinant DNA constructs to allow longer-term target gene suppression in cells are known in the art, including mammalian Pol III promoter systems (for example, H1 or U6/snRNA promoter systems (Tuschl, T. (2002) Nature Biotechnol. 20:446-448) capable of expressing functional double-stranded siRNAs; (Lee, N. S. et al. (2002) Nature Biotechnol. 20:500-505; Miyagishi, M. and Taira, K. (2002) Nature Biotechnol. 20:497-500; Paul, C. P. et al. (2002) Nature Biotechnol. 20:505-508; Yu, J.-Y. et al. (2002) Proc. Natl. Acad. Sci. USA 99(9):6047-6052; Sui, G. et al. (2002) Proc. Natl. Acad. Sci. USA 99(6):5515-5520).

Nucleic acids provided herein can include microRNA which can regulate gene expression at the post transcriptional or translational level. One common feature of miRNAs is that they are all excised from an approximately 70 nucleotide precursor RNA stem-loop, probably by Dicer, an RNase III-type enzyme, or a homolog thereof. By substituting the stem sequences of the miRNA precursor with miRNA sequence complementary to the target mRNA, a vector construct that expresses the novel miRNA can be used to produce siRNAs to initiate RNAi against specific mRNA targets in mammalian cells (Zheng, B. J. (2004) Antivir. Ther. 9:365-374). When expressed by DNA vectors containing polymerase III promoters, microRNA designed hairpins can silence gene expression, such as OPN expression.

Viral-mediated delivery mechanisms can also be used to induce specific silencing of targeted genes through expression of siRNA, for example, by generating recombinant adenoviruses harboring siRNA under RNA Pol II promoter transcription control (Xia et al. (2002) Nature Biotechnol. 20(10):1006-10). In vitro infection of cells by such recombinant adenoviruses allows for diminished endogenous target gene expression. Injection of recombinant adenovirus vectors into transgenic mice expressing the target genes of the siRNA results in in vivo reduction of target gene expression. In an animal model, whole-embryo electroporation can efficiently deliver synthetic siRNA into post-implantation mouse embryos (Calegari, F. et al. (2002) Proc. Natl. Acad. Sci. USA 99(22): 14236-40). In adult mice, efficient delivery of siRNA can be accomplished by the "high-pressure" delivery technique, a rapid injection (within 5 seconds) of a large volume of siRNA containing solution into animal via the tail vein (Lewis, D. L. (2002) Nature Genetics 32:107-108). Nanoparticles, liposomes and other cationic lipid molecules can also be used to deliver siRNA into animals. A gel-based agarose/liposome/siRNA formulation is also available (Jiamg, M. et al. (2004) Oligonucleotides 14(4):239-48).

Nucleic acids provided herein can include an antisense nucleic acid sequence selected such that it is complementary to the entirety of CXCR4 or CXCL12, a microRNA, or to a portion of CXCR4 or CXCL12 or a microRNA. In some embodiments, a portion can refer to at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, and at least about 80%, at least about 85%, at least about 90%, at least about 95%. In some embodiments, a portion can refer up to 100%. Examples of human CXCR4 and CXCL12 nucleic acid sequences useful with the methods provide herein are provided in Table 1 and also for CXCL12 in SEQ ID NOs: 08-10, and for CXCR4 in SEQ ID NO.: 11.

TABLE 1

Human CXCR4 mRNA transcript variant 1; Accession No. NM 001008540
(SEQ ID NO: 03)

```
   1   ttttttttct tccctctagt gggcggggca gaggagttag ccaagatgtg actttgaaac
  61   cctcagcgtc tcagtgccct tttgttctaa acaaagaatt ttgtaattgg ttctaccaaa
 121   gaaggatata atgaagtcac tatgggaaaa gatggggagg agagttgtag gattctacat
 181   taattctctt gtgcccttag cccactactt cagaatttcc tgaagaaagc aagcctgaat
 241   tggttttta aattgcttta aaaattttt ttaactgggt taatgcttgc tgaattggaa
 301   gtgaatgtcc attcctttgc ctcttttgca gatatacact tcagataact acaccgagga
 361   aatgggctca ggggactatg actccatgaa ggaacccgt ttccgtgaag aaaatgctaa
 421   tttcaataaa atcttcctgc ccaccatcta ctccatcatc ttcttaactg gcattgtggg
 481   caatggattg gtcatcctgg tcatgggtta ccagaagaaa ctgagaagca tgacggacaa
 541   gtacaggctg cacctgtcag tggccgacct cctctttgtc atcacgcttc ccttctgggc
 601   agttgatgcc gtggcaaact ggtactttgg aacttccta tgcaaggcag tccatgtcat
 661   ctacacagtc aacctctaca gcagtgtcct catcctggcc ttcatcagtc tggaccgcta
 721   cctggccatc gtccacgcca ccaacagtca gaggccaagg aagctgttgg ctgaaaaggt
 781   ggtctatgtt ggcgtctgga tccctgccct cctgctgact attcccgact tcatcttgc
 841   caacgtcagt gaggcagatg acagatata tctgtgaccgc ttctacccca tgacttgtg
 901   ggtggttgtg ttccagtttc agcacatcat ggttggcctt atcctgcctg gtattgtcat
 961   cctgtcctgc tattgcatta tcatctccaa gctgtcacac tccagggcc accagaagcg
1021   caaggccctc aagaccacag tcatcctcat cctggctttc ttcgcctgtt ggctgcctta
1081   ctacattggg atcagcatcg actccttcat cctcctggaa atcatcaagc aagggtgtga
1141   gtttgagaac actgtgcaca gtggatttc catcaccgag ccctagctt tcttccactg
1201   ttgtctgaac cccatcctct atgctttcct tggagccaaa tttaaaacct ctgcccagca
1261   cgcactcacc tctgtgagca gagggtccag cctcaagatc ctctccaaag gaaagcgagg
1321   tggacattca tctgttttcca ctgagtctga gtcttcaagt tttcactcca gctaacacag
1381   atgtaaaaga ctttttttta tacgataaat aactttttt taagttacac atttttcaga
1441   tataaaagac tgaccaatat tgtacagttt ttattgcttg ttggattttt gtcttgtgtt
1501   tctttagttt ttgtgaagtt taattgactt atttatataa attttttg tttcatattg
1561   atgtgtgtct aggcaggacc tgtggccaag ttcttagttg ctgtatgtct cgtggtagga
1621   ctgtagaaaa gggaactgaa cattccagag cgtgtagtga atcacgtaaa gctagaaatg
1681   atccccagct gtttatgcat agataatctc tccattcccg tggaacgttt ttcctgttct
1741   taagacgtga ttttgctgta gaagatggca cttataacca aagcccaaag tggtatagaa
1801   atgctggttt ttcagtttc aggagtgggt tgatttcagc acctacagtg tacagtcttg
1861   tattaagttg ttaataaaag tacatgttaa acttaaaaaa aaaaaaaaa aa
```

Human CXCL12 mRNA transcript variant 1; Accession No. NM 199168
(SEQ ID NO: 04)

```
   1   gccgcacttt cactctccgt cagccgcatt gcccgctcgg cgtccggccc ccgacccgcg
  61   ctcgtccgcc cgcccgcccg cccgcccgcg ccatgaacgc caaggtcgtg gtcgtgctgg
 121   tcctcgtgct gaccgcgctc tgcctcagcg acgggaagcc cgtcagcctg agctacagat
 181   gcccatgccg attcttcgaa agccatgttg ccagagccaa cgtcaagcat ctcaaaattc
 241   tcaacactcc aaactgtgcc cttcagattg tagcccggct gaagaacaac aacagacaag
 301   tgtgcattga cccgaagcta aagtggattc aggagtacct ggagaaagct ttaaacaagt
```

TABLE 1-continued

```
 361   aagcacaaca gccaaaaagg actttccgct agacccactc gaggaaaact aaaaccttgt
 421   gagagatgaa agggcaaaga cgtgggggag ggggccttaa ccatgaggac caggtgtgtg
 481   tgtggggtgg gcacattgat ctgggatcgg gcctgaggtt tgccagcatt tagaccctgc
 541   atttatagca tacggtatga tattgcagct tatattcatc catgccctgt acctgtgcac
 601   gttggaactt ttattactgg ggtttttcta agaaagaaat tgtattatca acagcatttt
 661   caagcagtta gttccttcat gatcatcaca atcatcatca ttctcattct cattttttaa
 721   atcaacgagt acttcaagat ctgaatttgg cttgtttgga gcatctcctc tgctcccctg
 781   gggagtctgg gcacagtcag gtggtggctt aacagggagc tggaaaaagt gtcctttctt
 841   cagacactga ggctcccgca gcagcgcccc tcccaagagg aaggcctctg tggcactcag
 901   ataccgactg gggctgggcg ccgccactgc cttcacctcc tctttcaacc tcagtgattg
 961   gctctgtggg ctccatgtag aagccactat tactgggact gtgctcagag accccctctcc
1021   cagctattcc tactctctcc ccgactccga gagcatgctt aatcttgctt ctgcttctca
1081   tttctgtagc ctgatcagcg ccgcaccagc cgggaagagg gtgattgctg gggctcgtgc
1141   cctgcatccc tctcctccca gggcctgccc cacagctcgg gccctctgtg agatccgtct
1201   ttggcctcct ccagaatgga gctggccctc tcctggggat gtgtaatggt cccctgctt
1261   acccgcaaaa gacaagtctt tacagaatca aatgcaattt taaatctgag agctcgcttt
1321   gagtgactgg gttttgtgat tgcctctgaa gcctatgtat gccatggagg cactaacaaa
1381   ctctgaggtt tccgaaatca gaagcgaaaa aatcagtgaa taaaccatca tcttgccact
1441   accccctcct gaagccacag cagggtttca ggttccaatc agaactgttg gcaaggtgac
1501   atttccatgc ataaatgcga tccacagaag gtcctggtgg tatttgtaac tttttgcaag
1561   gcattttttt atatatattt ttgtgcacat tttttttttac gtttctttag aaaacaaatg
1621   tatttcaaaa tatatttata gtcgaacaat tcatatattt gaagtggagc catatgaatg
1681   tcagtagttt atacttctct attatctcaa actactggca atttgtaaag aaatatatat
1741   gatatataaa tgtgattgca gcttttcaat gttagccaca gtgtattttt tcacttgtac
1801   taaaattgta tcaaatgtga cattatatgc actagcaata aaatgctaat tgtttcatgg
1861   tataaacgtc ctactgtatg tgggaattta tttacctgaa ataaaattca ttagttgtta
1921   gtgatggagc ttaaaaaaaa
```

Identifying Therapeutic Compounds

Some embodiments provided herein relate to methods for identifying therapeutic compounds. Some such embodiments for identifying therapeutic compounds which may be used to treat tumors, such as pancreatic tumors, can include contacting a target cell with a test compound and a CXCR4 agonist. Examples of CXCR4 agonists include CXCL12, SDF-1α (Sigma-Aldrich, St. Louis, Mo., USA), CTCE-0214 (peptide agonist of CXCR; amino acid sequence: KPVSLSYRAPFRFF-Linker-LKWIQEYLEKALN (SEQ ID NO:05); Chemokine Therapeutics Corp., Vancouver, Canada), CTCE-0021, and ATI-2341 (Faber, A., et al., J Biomed Biotechnol. 2007; 2007: 26065; Tudan, C., et al., J Med Chem. 2002 May 9; 45(10):2024-31; Pelus, L M., et al., Exp Hematol. 2005 March; 33(3):295-307; Tchernychev, B. et al., Proc Natl Acad Sci USA. 2010 Dec. 21; 107(51): 22255-9). The target cell can be contacted with the test compound and CXCR4 agonist simultaneously, at overlapping periods of time, or at different periods of time. In some embodiments, a target cell is contacted with the CXCR4 agonist prior to contacting the target cell with the test compound. In some embodiments, a target cell is contacted with the CXCR4 agonist during contacting the target cell with the test compound. In some embodiments, a target cell is contacted with the CXCR4 agonist prior to and during contacting the target cell with the test compound. Some embodiments also include determining whether the test compound significantly changes the level of expression or activity of a protein or a nucleic acid encoding a protein in the target cell. In some embodiments, the protein or nucleic acid encoding a protein is a protein or a nucleic acid encoding a protein whose level is changed by activation of CXCR4 by the CXCR4 agonist. In other words, the level or activity of the protein or nucleic acid encoding a protein is increased or decreased on contacting a cell with the CXCR4 agonist compared to the level or activity of the protein or nucleic acid encoding a protein in a cell not contacted with the CXCR4 agonist. In some embodiments, the level or activity of the protein or nucleic acid encoding the protein is increased or decreased by at least about 5%, 10%, 15%, 20%, 25%, 30%, 35%, 40%, 45%, 50%, 55%, 60%, 65%, 70%, 85%, 90%, 95%, 100%, or more. Examples of proteins and nucleic acids encoding proteins whose levels are changed by activation of CXCR4 include FAK, Akt, ERK, β-catenin, NF-κB, Bcl-2, Bcl-xL, Notch1, phosphorylated BAD, and SHH.

Some embodiments also include comparing the level or activity of the protein or a nucleic acid encoding a protein in a target cell contacted with a CXCR4 agonist and the test compound, to the level or activity of the protein or a nucleic acid encoding the protein in a target cell contacted with the CXCR4 agonist and not contacted with the test compound. Some embodiments also include determining whether the test compound decreases or increases the level or activity of the protein or a nucleic acid encoding a protein in the target cell. A decrease or increase in the level of expression or activity of a protein or level of a nucleic acid encoding a protein can be indicative that the test compound is a therapeutic compound. For example, a test compound that decreases the level of expression or activity of a protein or level of a nucleic acid encoding a protein whose level or activity is increased by activation of CXCR4 can be indicative of a therapeutic compound. Conversely, a test compound that increases the level of expression or activity of a protein or level of a nucleic acid encoding a protein whose level or activity is decreased by activation of CXCR4 can be indicative of a therapeutic compound. For example, compounds which change the level or activity of a protein or nucleic acid activated by activation of the CXCL12/CXCR4 pathway may be useful in decreasing resistance to chemotherapeutic drugs.

In an example embodiment, a target cell is contacted with a test compound and a CXCR4 agonist; the level of expression or activity of a protein or level of a nucleic acid encoding a protein whose level is increased by activation of CXCR4 is measured and compared to the level or activity of the protein or nucleic acid encoding the protein in a target cell contacted with the CXCR4 agonist and not contacted with the test compound. Any change in the level or activity of the protein or nucleic acid encoding the protein in a target cell is determined. A decrease in the level of expression or activity of a protein or level of a nucleic acid encoding a protein in the target cell contacted with a test compound and a CXCR4 agonist compared to a target cell contacted with the CXCR4 agonist and not contacted with the test compound is indicative that the test compound may be a therapeutic compound.

In an example embodiment, a target cell is contacted with a test compound and a CXCR4 agonist; the level of expression or activity of a protein or level of a nucleic acid encoding a protein whose level is decreased by activation of CXCR4 is measured and compared to the level or activity of the protein or nucleic acid encoding the protein in a target cell contacted with the CXCR4 agonist and not contacted with the test compound. Any change in the level or activity of the protein or nucleic acid encoding the protein in a target cell is determined. An increase in the level of expression or activity of a protein or level of a nucleic acid encoding a protein in the target cell contacted with a test compound and a CXCR4 agonist compared to a target cell contacted with the CXCR4 agonist and not contacted with the test compound is indicative that the test compound may be a therapeutic compound.

In some embodiments the target cell comprises a mammalian cell, such as a human cell. In some embodiments, the target cell comprises a pancreatic cell. In some embodiments the target cell comprises a tumor cell. In some embodiments, the target cell comprises a pancreatic tumor cell. In some embodiments, the target cell comprises a cell selected from a pancreatic tumor cell line, such as CFPAC-1, AsPc-1, SW1990, Colo-357, MiaPaCa, Panc1, Panc02.37, Panc10.05, BxPC3, Panc02.03, HPAF-II, and CaPan-1.

Examples of test compounds and potential therapeutic compounds include small molecules (including but not limited to organic chemical compounds which have been obtained from natural sources or synthesized), nucleic acids (including but not limited to antisense nucleic acids, ribozymes, or siRNAs), peptides and proteins.

Methods to measure the levels or activities of a protein or a nucleic acid in a target cell are well known in the art. Examples of methods to measure the levels and activities of proteins include Western analysis, various biological assays, ELISAs and the like. For example, measurement of protein levels may utilize binding agents. There are a variety of assay formats known to those of ordinary skill in the art for using a binding agent to detect protein markers in a sample. See, for example, Harlow and Lane, Antibodies: A Laboratory Manual, Cold Spring Harbor Laboratory, 1988. In a preferred embodiment, an assay involves the use of binding agent immobilized on a solid support to bind to the polypeptide in the sample. The bound polypeptide may then be detected using a detection reagent that contains a reporter group and specifically binds to the binding agent/polypeptide complex. Such detection reagents may comprise, for example, a binding agent that specifically binds to the polypeptide or an antibody or other agent that specifically binds to the binding agent, such as an anti-immunoglobulin, protein G, protein A or a lectin. In such embodiments, the binding agent can comprise an antibody or fragment thereof specific to a particular protein. In some embodiments, the assay is a two-antibody sandwich assay. This assay may be performed by first contacting an antibody that has been immobilized on a solid support, commonly the well of a microtiter plate, with the sample, such that polypeptides within the sample are allowed to bind to the immobilized antibody. Unbound sample is then removed from the immobilized polypeptide-antibody complexes and a detection reagent (preferably a second antibody capable of binding to a different site on the polypeptide) containing a reporter group is added. The amount of detection reagent that remains bound to the solid support is then determined using a method appropriate for the specific reporter group.

Examples of methods to measure the level of a nucleic acid are well known and include Southern analysis, Northern analysis, Q-RT-PCR (quantative realtime PCR), and the like. For example, techniques for both PCR based assays and hybridization assays are well known in the art (see, for example, Mullis et al., Cold Spring Harbor Symp. Quant. Biol., 51:263, 1987; Erlich ed., PCR Technology, Stockton Press, NY, 1989). Methods of real-time quantitative PCR or RT-PCR using TaqMan probes are well known in the art and are described in for example, Heid et al. 1996, Real time quantitative PCR, Genome Res., 10:986-994; and Gibson et al., 1996, A novel method for real time quantitative RT-PCR, Genome Res. 10:995-1001.

Kits

Some embodiments provided herein relate to kits for identifying a therapeutic agent. Some such embodiments include a CXCL12 inhibitor; and an isolated tumor cell.

In some embodiments, the CXCL12 inhibitor comprises a CXCR4 antagonist. In some embodiments, the CXCR4 antagonist is selected from the group consisting of Plerixafor (AMD3100), BKT140, TN14003, CTCE-9908, KRH-2731, TC14012, KRH-3955, and AMD070. In some embodiments, the CXCR4 antagonist comprises Plerixafor (AMD3100).

In some embodiments, the cell comprises a pancreatic cell. In some embodiments, the cell is selected from the group consisting of CFPAC-1, AsPc-1, SW1990, Colo-357, MiaPaCa, Panc1, Panc02.37, Panc10.05, BxPC3, Panc02.03, HPAF-II, and CaPan-1.

In some embodiments, the cell comprises a mammalian cell. In some embodiments, the cell comprises a human cell.

EXAMPLES

Example 1

CXCL12/CXCR4 Signaling in Pancreatic Cells

Cell Lines and Culture Conditions

Human pancreatic cancer cell lines (Colo357, SW1990, AsPc1, BxPc3, CaPan1, HPAF II, CFPACI, Panc1, MiaPaCa2, Panc10.05, Panc03.27, Panc02.03) were purchased from the American Type Culture Collection (Manassas, Va.). The cell lines were maintained in culture as adherent monolayer in RPMI-1640 or Dulbecco's Modified Eagle Medium (DMEM) (Thermo Scientific, Logan, Utah) supplemented with 10% fetal bovine serum (FBS) (Atlanta Biologicals, Lawrenceville, Ga.) and 100 µM each of penicillin and streptomycin (Invitrogen, Carlsbad, Calif.). Cells were grown at 37° C. with 5% $CO_2$ in a humidified atmosphere.

Reagents and Antibodies

SuperScript™ II Reverse Transcriptase and Vybrant MTT cell proliferation assay kits were from Invitrogen. Recombinant human CXCL12 and CXCL12 ELISA kit was purchased from R&D Systems (Minneapolis, Minn.). AMD3100 octahydrochloride and anti-β-actin mouse monoclonal antibody were purchased from Sigma-Aldrich (St. Louis Mo.). Gemcitabine was provided by USAMCI pharmacy. Phosphatase and protease inhibitors and FuGENE transfection reagent were from Roche Diagnostics (Mannheim, Germany). Antibody against CXCR4 (rabbit polyclonal) was from Abcam (Cambridge, Mass.). Anti-Akt, -pAkt and -pFAK (rabbit monoclonal) antibodies were from Epitomics (Burlingame, Calif.). Antibodies for ERK1/2 (rabbit monoclonal), pERKllZ (mouse monoclonal), Bcl-2 (rabbit polyclonal), BAD (rabbit polyclonal), pBAD (rabbit polyclonal), Bcl-xL (rabbit monoclonal), FAK (rabbit polyclonal), and Survivin (rabbit monoclonal) were from Cell Signaling Technologies (Beverly, Mass.). The Notch1 (goat polyclonal) and secondary horseradish peroxidase-conjugated anti-rabbit, anti-mouse and antigoat antibodies were purchased from Santa Cruz Biotechnology (Santa Cruz, Calif.). DNAzol reagent was from Molecular Research (Cincinnati, Ohio). CaspACE FITC-VAD-FMK and Dual Luciferase Assay System kit were from Promega (Madison, Wis.). ECL Plus Western Blotting detection kit was from Thermo Scientific (Logan, Utah). LY294002 and PD98059 (PI3K and MEK1 inhibitors, respectively) were purchased from Cell Signaling Technology. TOPflash or FOPflash reporter plasmids were kindly provided by Dr. R. Samant, USAMCI, and pGL4.32[luc2P/NF-κB-RE/Hygro] reporter plasmid was purchased from Promega.

Western Blot Analysis

Cells were processed for protein extraction and western blotting using standard procedures. Briefly, cells were washed twice with PBS and scraped into NP-40 lysis buffer containing protease and phosphotase inhibitors. Cell lysates were passed through a needle syringe to facilitate the disruption of the cell membranes and were centrifuged at 14,000 rpm for 20 min at 4° C., and supernatants were collected. Proteins (10-50 µg) were resolved by electrophoresis on 10% SDS-PAGE, transferred onto polyvinylidene difluoride (PVDF) membrane and subjected to standard immunodetection procedure using specific antibodies: AKT, pAKT ERK1/2, pERK1/2, Bcl-2, Bcl-xL, FAk, pFAk, Survivin, β-catenin and BAD (1:1000), pBAD (1:500), Notch-1 (1:200) and β-actin (1:20000). All secondary antibodies were used at 1:2500 dilutions. Blots were processed with ECL Plus Western Blotting detection kit and the signal detected using an LAS-3000 image analyzer (Fuji Photo Film Co., Tokyo, Japan).

Enzyme-Linked Immunosorbent Assay (ELISA)

Cells ($1 \times 10^6$) were seeded in six-well plate containing growth medium supplemented with FBS and cultured overnight. After 24 h, growth media was removed, and cells conditioned in serum free medium for next 72 hours. The culture media were then collected, centrifuged at 1500 rpm for 5 min to remove particles, and supernatants frozen at −80° C. until use. CXCL12 was measured using an ELISA kit according to the manufacturer's instructions.

LEF/TCF and NF-κB Transcriptional Activity Assays

To measure the LEF/TCF and NF-κB transcriptional activity, pancreatic cancer cells ($1 \times 10^5$) were seeded in 12-well plates. After 24 h incubation, cells were transiently transfected with the luciferase promoter-reporter constructs (TOP flash, FOPflash or pGL4.32[luc2P/NF-kB-RE/Hygro]. TOPflash reporter plasmid contains three copies of the Tcf/Lef sites upstream of a thymidine kinase (TK) promoter and the Firefly luciferase gene, while in FOPflash, Tcf/Lef sites are mutated and therefore it serves as a control for measuring nonspecific activation of the reporter. Cells were also co-transfected with a reporter plasmid, containing *Renilla reniformis* luciferase gene downstream of the TK promoter, to control for the transfection efficiency. All transfections were performed using FuGene as a transfection reagent according to the manufacturers' recommendations. Cells were treated with CXCL12 (100 ng) 24 h post TOPflash/FOPflash or pGLA.32[luc2P/NF-kB-RE/Hygro] transfection, and after the next 24 h, total protein was isolated in passive lysis buffer. Luciferase activity was measured using the Dual Luciferase Assay System. All experiments were done in triplicate and relative luciferase activity reported as the fold induction after normalization for transfection efficiency.

Cell Viability Assay

Panc1 and MiaPaCa cells were seeded in 96-wells plate at a density of 5000 cells/well, followed by next day treatment with increasing concentration of gemcitabine (0-10 µM) in presence or absence of CXCL12 (100 ng/mL). After 72 h of treatment, cell growth was determined by using Vybrant MIT cell proliferation assay. Growth was calculated as percent $(\%)=[\{(A/B)-1\} \times 100]$, where A and B are the absorbance of treatment and control cells, respectively. To examine the effect of CXCR4 targeting, cells were pre-incubated with small molecule CXCR4 antagonist, AMD3100 (5 µg/mL), for 1 h. To delineate the role of Akt and ERK pathways, cells were pretreated for 1 h with LY294002 (20 µM) and PD98059 (25 µM), respectively.

DNA Fragmentation Assay

Panc1 and MiaPaca cells were cultured in 10% DMEM with and without gemcitabine (5 and 10 µM) and CXCL12 (100 ng/mL) for 48 h. Cells were washed twice with phosphate buffer saline (PBS) and DNA was extracted using DNAzol reagent. 2 µg of isolated DNA was resolved on 1.0% agarose gel containing ethidium-bromide (EtBr) and observed under a LAS-3000 image analyzer (Fuji Photo Film Co.).

Measurement of Apoptosis In Situ

Panc1 and MiaPaCa cells were cultured on chamber slides and treated with gemcitabine and/or CXCL12 as described previously. Apoptosis was detected by staining the cells with CaspACE FITC-VAD-FMK solution in PBS for 2 h at 37° C. CaspACE™ FITC-VAD-FMK In Situ Marker is a fluorescent analog of the pan-caspase inhibitor Z-VAD-FMK (carbobenzoxy-valyl-alanylaspartyl-[O-methyl]-fluoromethylketone), which irreversibly binds to activated caspases and is a surrogate for caspase activity in situ. Following staining with CaspACE FITC-V AD-FMK, cells were fixed with 4% paraformaldehydede at room temperature and washed with PBS. The bound fluorescent marker was detected under a Nikon Eclipse TE2000-U fluorescent microscope (Nikon Instruments Inc, Melville, N.Y.).

Statistical Analysis

Each experiment was performed at least three times and all the values were expressed as mean±SD. The differences between the groups were compared using student's t-tests. A p value of equal or less than 0.05 was considered statistically significant.

Results

Figure 1:
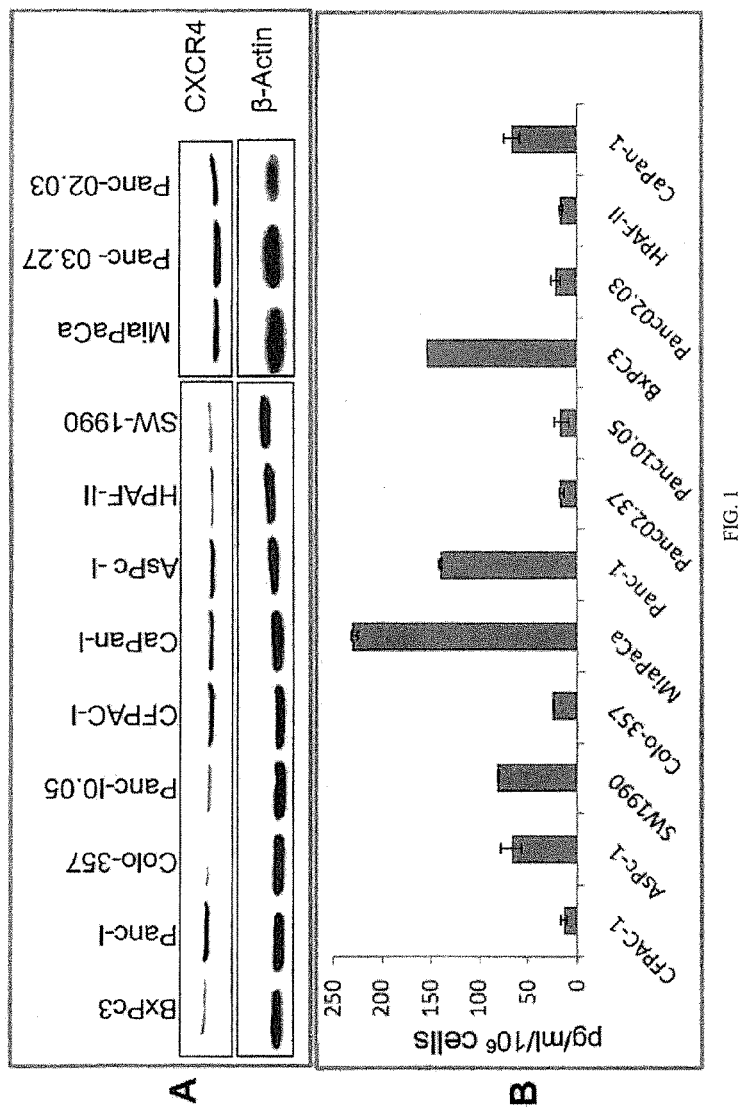
FIG. 1 (panels A-C) relates to CXCR4 and CXCL12 expression and growth response in pancreatic cancer cells.
Figure 1:
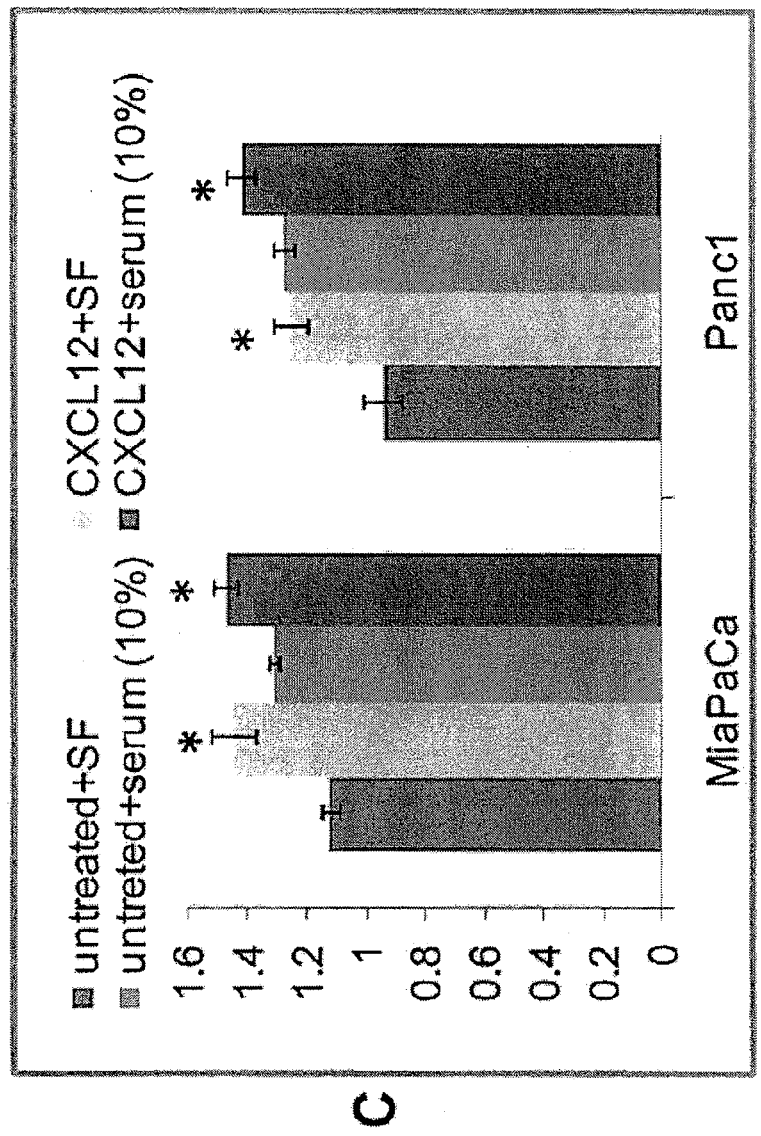

Expression of CXCR4 and CXCL12 in Pancreatic Cancer Cells and their Growth Responsiveness to CXCL12 Stimulation CXCR4 is overexpressed in pancreatic tumor tissues and premalignant lesions (Marechal et al., 2009; Thomas et al., 2008). In addition, CXCR4 is also expressed by the pancreatic cancer stem cells (Hermann et al., 2007). The expression of CXCR4 and its ligand CXCL12 by immunoblot and enzyme-linked immunosorbant assay were examined, respectively, in a panel of twelve pancreatic cancer cell lines. The data showed that all pancreatic cancer cell lines examined express CXCR4 and low levels of CXCL12 (13-230 pg/mL/$10^6$ cells) (FIG. 1 panel A, and FIG. 1 panel B). Growth responsiveness of pancreatic cancer cells to CXCL12 stimulation in two poorly differentiated pancreatic cancer cell lines, MiaPaCa and Panc1 was also tested. The cells were treated with CXCL12 in serum-free and serum containing culture media. In absence of serum growth factors, CXCL12 stimulation led to the 29-33% induction of growth in pancreatic cancer cells, while a moderate increase (11-13%) were observed in presence of serum growth factors (FIG. 1 panel C). These findings suggest that CXCL12-CXCR4 signaling is active in pancreatic cancer cells and can impact tumor cell growth.

Figure 2A:
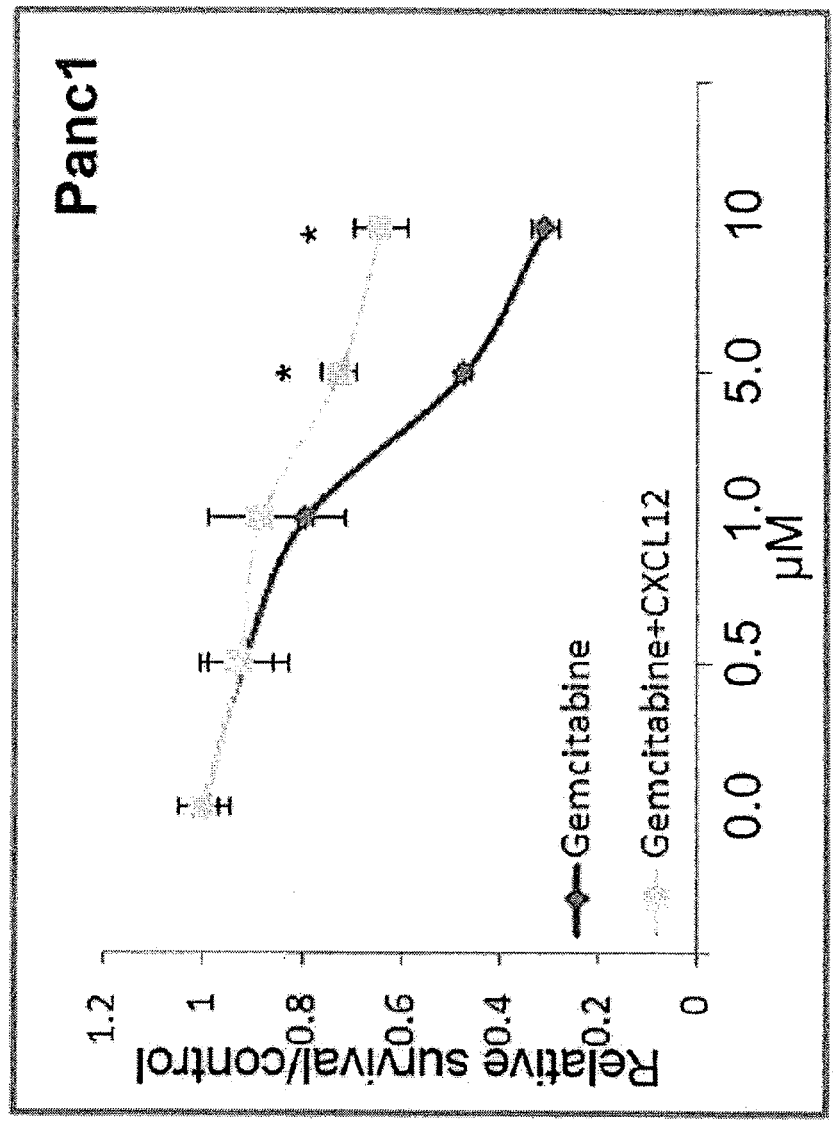
FIGS. 2A and 2B relate to relative survival of pancreatic cancer cells and rescue of cells from gemcitabine-induced toxicity upon CXCL12 treatment.
Figure 2B:
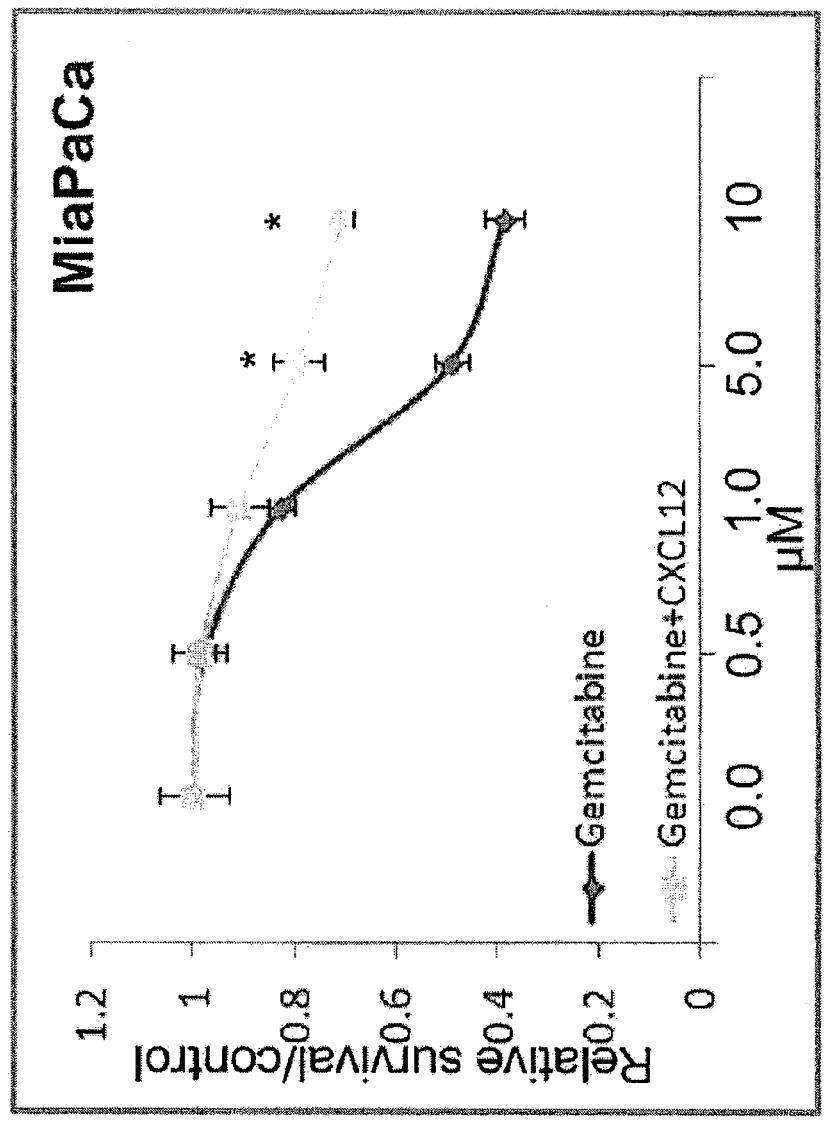

CXCR4 Activation Rescues Pancreatic Cancer Cells from Gemcitabine-induced Cytotoxicity Although the data indicated minimal expression of CXCL12 by pancreatic cancer cells (FIG. 1 panel B), it is reported to be expressed at high levels by stromal cells and at sites of pancreatic cancer metastasis (Matsuo et al., 2009; Saur et al., 2005; Mori et al., 2004). Therefore, CXCL12-CXCR4 signaling might act in paracrine manner to influence pancreatic tumor growth and other malignant properties. In view of the fact that pancreatic cancer cells are highly resistant to chemotherapy, and gemcitabine is only minimally effective against this malignancy, the role of CXCL12-CXCR4 signaling axis in pancreatic cancer chemo-resistance was investigated. Pancreatic cancer cells (Panc1 and MiaPaCa) were treated with various doses of gemcitabine (0-10 μM) in the presence and absence of CXCL12 (100 ng/mL) in serum-containing media. The data shows that CXCL12 treatment induced significant resistance ($p<0.05$) to gemcitabine-cytotoxicity in both pancreatic cancer cell lines tested (FIG. 2A and FIG. 2B). At 5.0 μM gemcitabine, 52.3% and 50.7% cytotoxicity was observed in Panc1 and MiaPaCa cells, respectively, as compared to untreated cells. In contrast, only 27.1% and 20.5% gemcitabine cytotoxicity, respectively, was reported in cells co-treated with CXCL12, indicating a significant survival advantage.

Figure 3:
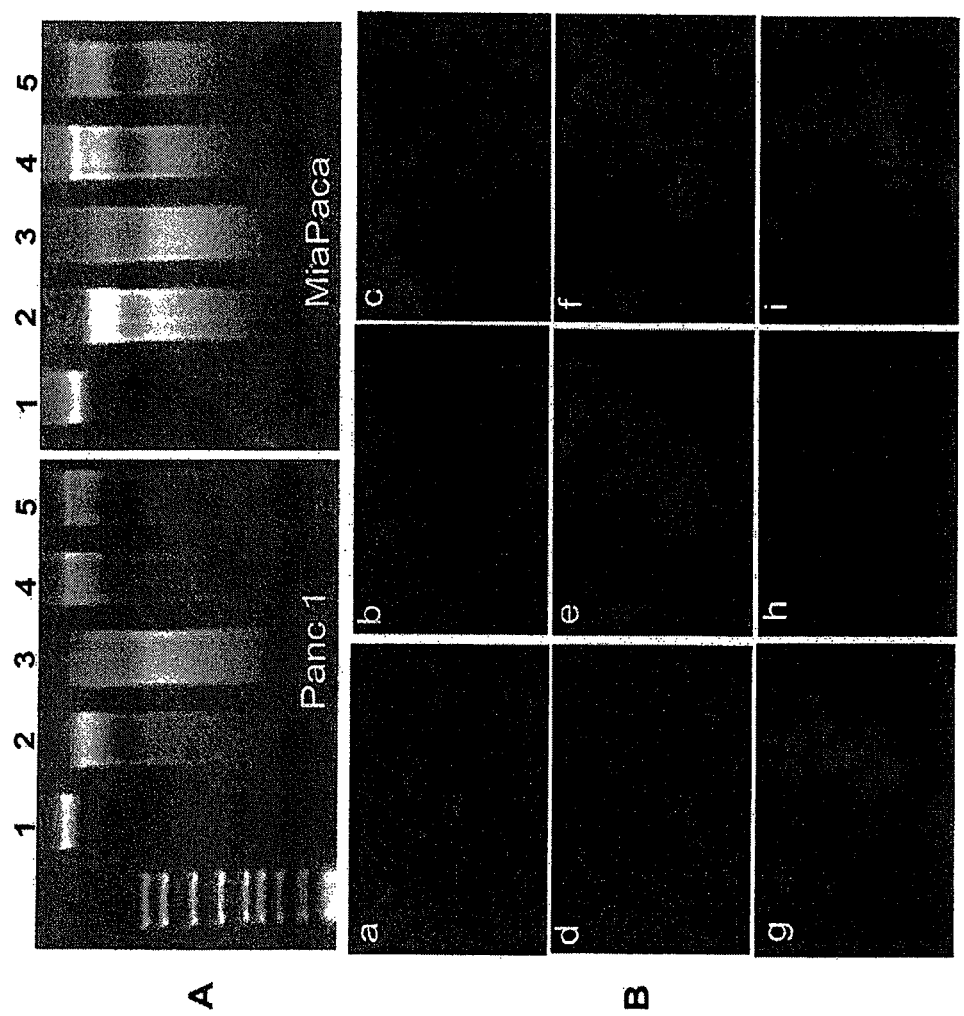
FIG. 3 (panels A and B) relates to anti-apoptotic effects of CXCL12 treatment on gemcitabine-induced cell death.

To examine whether CXCL12-induced chemo-resistance was due to its antiapoptotic effects on pancreatic cancer cells, DNA fragmentation and caspase activity was analyzed. The data demonstrate that CXCL12-treated cells have reduced DNA fragmentation (FIG. 3 panel A) and enhanced activity of caspases (FIG. 3 panel B) compared to cells treated with gemcitabine alone. These findings strongly suggest that CXCL12 treatment prevents apoptosis of pancreatic cancer cells by gemcitabine and suggest the implication of CXCL12-elicited survival pathways.

CXCL12 Treatment Leads to FAK, Akt and ERK Activation

In next set of experiments, the potential survival signaling pathways that might mediate the CXCL12-elicited chemo-resistance were examined. Because G-protein-coupled receptors transducer signals via diverse signaling pathways including activation of focal adhesion kinase (FAK), PI3K/Akt and ERK (Rozengurt, 2007), the activation of these signaling molecules in response to CXCL12-treatment was investigated. Pancreatic cancer cells (Panc1 and MiaPaCa) were briefly treated with CXCL12 (5-30 min) and activation of FAK, Akt and ERK was examined by immuno-probing of total protein with phospho-form specific antibodies. The data revealed significant activation of all the three effector proteins in response to CXCL12 treatment (FIG. 4). Both Akt and ERK have been shown to promote survival by phosphorylating BAD (a proapoptotic member of the Bcl-2 family) and thereby controlling its association with Bcl-xL or Bcl-2 (anti-apoptotic members of the family) (Sheridan et al., 2008; Scheid and Duronio, 1998; Datta et al., 1997). Therefore, the change in BAD phosphorylation in CXCL12-treated pancreatic cancer cells was examined. The data showed an increased level of phospho-BAD in both Panel and MiaPaCa cell lines treated with CXCL12 (FIG. 4) suggesting that it could be one of the mechanisms by which CXCL12-CXCR4 signaling axis protects the pancreatic cancer cells from apoptosis.

Enhanced Transcriptional Activities of β-catenin and NF-κB and Induction of Survival Proteins by CXCL12 Treatment of Pancreatic Cancer Cells In addition to directly influencing apoptotic signaling via BAD phosphorylation, both Akt and ERK can have indirect impacts on cell survival. The indirect routes involve the activation of β-catenin and NF-κB that can elicit the expression of survival proteins. Therefore, the transcriptional activities of β-catenin and NF-κB responsive promoters after CXCL12 treatment in pancreatic cancer cells were examined. Luciferase reporter assays indicated modest induction of transcriptional activity of β-catenin [2.05 fold (Panc1) and 1.92 fold (MiaPaCa)] and NF-κB responsive promoter [2.98 fold (Panc1) and 2.26 fold (MiaPaCa)] in CXCL12-treated cells (FIG. 5 panel A). As activation of β-catenin and NF-κB may culminate in the induction of important survival genes, the expression of target pro-survival and anti-apoptotic proteins were examined. The data showed that the expression of Bcl-2, Bcl-xL, Notch-1 and survivin proteins was significantly induced in response to CXCL12 treatment of pancreatic cancer cells (FIG. 5 panel B). These results suggest that the upregulation of key survival proteins may be another mechanism by which CXCL12-CXCR4 signaling axis protects the pancreatic cancer cells from gemcitabine induced apoptotic cell death.

Small Molecule CXCR4 Antagonist, AMD3100, Abrogates CXCL12-induced Growth and Gemcitabine-resistance in Pancreatic Cancer Cells Having observed a role of CXCR4 activation in gemcitabine-resistance and potentiation of survival pathways, whether the small molecule CXCR4 antagonist, AMD3100, could diminish CXCL12-induced chemo-resistance in pancreatic cancer cells was investigated. In addition, pharmacological inhibitors of Akt (LY294002) and ERK (PD98059) signaling pathways were utilized, to delineate their role in the CXCL12-induced anti-apoptotic response. Pancreatic cancer cells were treated for 1 h with AMD3100, LY294002, and PD98059 prior to treatment with CXCL12 alone or in combination with gemcitabine. Pre-treatment with AMD3100 abolished the CXCL12-induced cell signaling, growth promotion and chemo-resistance of pancreatic cancer cells (FIG. 6 panel A, and FIG. 6 panel B). While both the inhibition of Akt and ERK pathways had a significant negative impact on CXCL12-induced chemoresistance, a more potent effect of blockade of Akt signaling was observed (FIG. 6 panel B). These findings indicate that CXCL12-mediated survival response is signaled through the CXCR4 and mediated via the activation of Akt and ERK signaling pathways. This is particularly important considering the expression of a novel CXCL12 receptor, CXCR7, in pancreatic cancer cells at least at the transcript level (data not shown).

Discussion

Pancreatic cancer, in most cases, is diagnosed late, when it has already advanced locally or metastasized to distant sites (Singh et al., 2004). Under this scenario, chemotherapy is the only treatment option. However, resistance to chemotherapy is a major clinical problem in pancreatic cancer and gemcitabine, the only FDA approved drug for pancreatic cancer therapy improves the patients' survival by only two weeks (Olive et al., 2009). Therefore, understanding the mechanisms of drug-resistance in pancreatic cancer is a major focus in pancreatic cancer research to facilitate the development of novel therapeutic approaches or improve current therapy. Chemokine signaling has long been implicated in cancer progression and metastasis through autocrine or paracrine mechanisms (Singh et al., 2007). Importantly, in previous studies, a chemokine receptor, CXCR4, was shown to be overexpressed in pancreatic cancer tissues and cancer stem cells (Marechal et al., 2009; Thomas et al., 2008; Hermann et al., 2007) and has been shown to potentiate pancreatic cancer growth and invasion (Marchesi et al., 2004; Mori et al., 2004; Hermann et al., 2007). Another aspect of this signaling node in protecting pancreatic cancer cells from chemotherapeutic drug-induced apoptosis was investigated. All the pancreatic cancer cell lines tested expressed CXCR4, but low levels of CXCL12. Nonetheless, significant protection of pancreatic cancer cells from gemcitabine toxicity was observed upon co-treatment with exogenous CXCL12 indicating a role for CXCL12-CXCR4 signaling axis in pancreatic cancer chemo-resistance. As CXCL12 is abundantly expressed by stromal cells (Matsuo et al., 2009), this could be an exemplary example for the role of tumor microenvironment interaction in modulating the therapeutic response. To gain an insight into the mechanistic basis for the protective effects, the activation of downstream signaling pathways was examined. Consistent with previous reports (Lu et al., 2009; Shen et al., 2010; Glodek et al., 2007), CXCL12 induced the activation of FAK, Akt and ERK. In a recent study, activation of FAK by extracellular matrix (ECM)-integrin signaling was shown to promote the chemoresistance of pancreatic cancer cells (Huanwen et al., 2009). Akt and ERK have also been shown to promote survival signaling (Middleton et al., 2008), and constitutive or induced activation of ERK and Akt pathways has been previously associated with chemo-resistant behavior of pancreatic cancer cells (Zhao et al., 2006; Yokoi and Fidler, 2004). In fact, FAK associated chemo-resistance of pancreatic cancer cells was shown to be mediated, in part, by the activation of PI3KJAkt pathway (Huanwen et al., 2009).

Both Akt and ERK can transduce survival signals directly or indirectly. In direct course, Akt and ERK have been shown to phosphorylate BAD, a pro-apoptotic member of the Bcl-2 family (Sheridan et al., 2008; Scheid and Duronio, 1998; Datta et al. 1997). Phosphorylation prevents BAD from binding either Bcl-2 or Bcl-xL and thus suppresses apoptosis. In the indirect route, induction of survival protein expression occurs via activation of β-catenin and NF-κB pathways. Activation of ERK has been shown to promote transactivation of β-catenin by phosphorylating α-catenin (Ji et al., 2009). Furthermore, Akt can activate 3-catenin by inducing direct phosphorylation or by inactivating GSK-3 (3 (Fang et al., 2007; Monick et al., 2001; Korkaya et al., 2009). In other reports, Akt pathway has been shown to regulate NF-κB, and NF-κB was shown to be essential for oncogenic transformation by PI3K and Akt (Sizemore et al., 1999; Romashkova and Makarov, 1999; Ozes et al., 1999; Madrid et al., 2000). Akt-induced activation of NF-κB likely occurs via phosphorylation of IKKα, which then targets the IκB inhibitor protein as well as phosphorylates the p65 NF-κB subunit (Ozes et al., 1999; Madrid et al., 2000; Bai et al., 2009). Consistent with these findings, enhanced transcriptional activities of β-catenin and NF-κB responsive promoters and expression of downstream targets in CXCL12-treated pancreatic cancer cells was observed. Enhanced transcriptional activity of β-catenin and NF-κB has been shown to induce epithelial to mesenchymal transition (EMT) and in recent studies, EMT has been associated with drug-resistant nature of pancreatic cancer cells (Li et al., 2009; Wang et al., 2009). In fact, relative drug-resistant nature of pancreatic cancer cells has been correlated with the mesenchymal phenotype (Shah et al., 2007). Other studies have shown that the underlying resistance to apoptosis is, in part, due to constitutive activation of NF-κB in pancreatic cancer (Wang et al., 2010; Harikumar et al., 2010). Our results also indicate that the CXCL12-induced gemcitabine resistance in pancreatic cancer cells might, in part, also be due to the activation of NF-κB and induction of downstream survival proteins (Bcl-2, Bcl-xL, survivin, etc.). The use of small-molecule inhibitors represents an attractive targeted therapeutic approach.

AMD3100, a specific antagonist of CXCR4, was utilized to target CXCR4 activation in response to CXCL12 treatment and demonstrate its efficacy in abolishing the chemoprotective effect of CXCL12-CXCR4 signaling axis. The therapeutic potential of AMD3100 has been studied largely in fighting HIV infection (De, 2003), although there are also some recent reports that highlight its therapeutic use in cancer (Azab el al., 2009; Yasumoto et al., 2006). In the same line, the data also indicate that AMD3100 might be useful in targeting the CXCL12-CXCR4 signaling axis in pancreatic cancer. Pharmacokinetics and safety of AMD3100 has been studied in human volunteers after intra-venous injection and shown to have minimal side effects (Hendrix et al., 2000). Therefore, AMD3100 can serve as a novel therapeutics for pancreatic cancer alone or in combination with cytotoxic drug.

In conclusion, the findings provide additional support for the pathological role of CXCL12-CXCR4 signaling in pancreatic cancer, and demonstrate, for the first time, a role for this axis in drug-resistance. The data shows that the induced chemo-resistance is partly mediated by the activation of Akt and ERK signaling pathways and a small molecule antagonist against CXCR4 can effectively abrogate the survival signals and re-sensitize the pancreatic cancer cells to gemcitabine cytotoxicity. Therefore, future clinical trials in pancreatic cancer might benefit from targeting of this signaling axis alone or in combination with chemotherapy.

Example 2

Time Course of CXCL12-induced Sonic Hedgehog (SHH) Expression

Panc1 and MiaPaCa cells were treated with CXCL12 and expression of SHH was measured by Q-RT-PCR and Western blot analysis.

Q-RT-PCR: Pancreatic cancer cells (Panc1 and MiaPaCa) were treated with CXCL12 for different time point (0, 4, 8, 24, 48 hours) for Q-RT-PCR analysis. To confirm the induced expression of sonic hegedehog (SHH), reverse transcriptase based-PCR (RT-PCR) analysis was performed, using SHH-specific primers. Briefly, cDNA was synthesized from 5 μg total RNA using SuperScript™ II Reverse Transcriptase (Invitrogen) and oligo(dT) primer. Two micro liter of first strand cDNA (1:10 dilution) was amplified using the SHH specific and GAPDH specific primers control. Amplified products were resolved through a 1.5% agarose gel containing ethidium bromide and analyzed using an Alpha Imager gel documentation system (Alphalnnotech, San Leandro, Calif.).

Immunoblot analyses: NP-40 lysis buffer containing protease and phosphatase inhibitors (Roche Diagnostics. 50 μg protein was resolved by SDS-PAGE (8-12%). The primary antibodies were: anti-sonic hedgehog (SHH, 1:2000, rabbit monoclonal, Millipore. Secondary antibody (Santa Cruz Biotechnology) was horseradish peroxidase (HRP)-conjugated and was used a 1:2000 dilution. Bound immunocomplexes were detected using ECL Plus chemiluminescent detection reagent (GE Healthcare, Piscataway, N.J.).

Treatment of Panc1 cells and MiaPaCa cells with CXCL12 induced expression of SHH (FIG. 7).

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention. Each of the following references is incorporated herein by reference in its entirety:

REFERENCES

Azab A K, et al., (2009) CXCR4 inhibitor AMD3100 disrupts the interaction of multiple myeloma cells with the bone marrow microenvironment and enhances their sensitivity to therapy. Blood 113 (18): 4341-4351

Bai D, Ueno L, Vogt P K (2009) Akt-mediated regulation of NFkappaB and the essentialness of NFkappaB for the oncogenicity of PI3K and Akt. Int J Cancer 125 (12): 2863-2870

Datta S R, Dudek H, Tao X, Masters S, Fu H, Gotoh Y, Greenberg M E (1997) Akt phosphorylation of BAD couples survival signals to the cell-intrinsic death machinery. Cell 91 (2): 231-241

De C E (2003) The bicyclam AMD3100 story. Nat Rev Drug Discov 2 (7): 581-587

Fang D, Hawke D, Zheng Y, Xia Y, Meisenhelder J, Nika H, Mills G B, Kobayashi R, Hunter T, Lu Z (2007) Phosphorylation of beta-catenin by AKT promotes beta-catenin transcriptional activity. J Biol Chem 282 (15): 11221-11229

Gelmini S, Mangoni M, Serio M, Romagnani P, Lazzeri E (2008) The critical role of SDFIICXCR4 axis in cancer and cancer stem cells metastasis. J Endocrinol Invest 31 (9): 809-819

Glodek A M, Le Y, Dykxhoorn D M, Park S Y, Mostoslavsky G, Mulligan R, Lieberman J, Beggs H E, Honczarenko M, Silberstein L E (2007) Focal adhesion kinase is required for CXCL12-induced chemotactic and pro-adhesive responses in hematopoietic precursor cells. Leukemia 21 (8): 1723-1732

Harikumar K B, Kunnumakkara A B, Sethi G, Diagaradjane P, Anand P, Pandey M K, Gelovani J, Krishnan S, Guha S, Aggarwal B B (2010) Resveratrol, a multi targeted agent, can enhance antitumor activity of gemcitabine in vitro and in orthotopic mouse model of human pancreatic cancer. Int J Cancer 127 (2): 257-268

Hendrix C W, Flexner C, MacFarland R T, Giandomenico C, Fuchs E J, Redpath E, Bridger G, Henson G W (2000) Pharmacokinetics and safety of AMD-3100, a novel antagonist of the CXCR4 chemokine receptor, in human volunteers. Antimicrob Agents Chemother 44 (6): 1667-1673

Hermann P C, Huber S L, Herrier T, Aicher A, Ellwart J W, Guba M, Bruns C J, Heeschen C (2007) Distinct populations of cancer stem cells determine tumor growth and metastatic activity in human pancreatic cancer. Cell Stem Cell I (3): 313-323

Huanwen W, Zhiyong L, Xiaohua S. Xinyu R, Kai W, Tonghua L (2009) Intrinsic chemoresistance to gemcitabine is associated with constitutive and laminin-induced phosphorylation of FAK in pancreatic cancer cell lines. Mol Cancer 8:125. 125

Jemal A, Siegel R, Ward E, Hao Y, Xu J, Thun M J (2009) Cancer statistics, 2009. CA Cancer J Clin 59 (4): 225-249

Ji H, Wang J, Nika H, Hawke D, Keezer S, Ge Q, Fang B, Fang X, Fang D, Litchfield D W, Aldape K, Lu Z (2009) EGF-induced ERK activation promotes CK2-mediated disassociation of alpha-Catenin from beta-Catenin and transactivation of beta-Catenin. Mol Cell 36 (4): 547-559

Korkaya H, Paulson A, Charafe-Jauffret E, Ginestier C, Brown M, Dutcher J, Clouthier S G, Wicha M S (2009) Regulation of mammary stem/progenitor cells by PTEN/Akt/beta-catenin signaling. PLoS Biol 7 (6): e1000121

Koshiba T, Hosotani R, Miyamoto Y, Ida J, Tsuji S, Nakajima S, Kawaguchi M, Kobayashi H, Doi R, Hori T, Fujii N, Imamura M (2000) Expression of stromal cell-derived factor I and CXCR4 ligand receptor system in pancreatic cancer: a possible role for tumor progression. Clin Cancer Res 6 (9): 3530-3535

Li Y, VandenBoom T G, Kong D, Wang Z, Ali S, Philip P A, Sarkar F H (2009) Up-regulation of miR-200 and let-7 by natural agents leads to the reversal of epithelial-to-mesenchymal transition in gemcitabine-resistant pancreatic cancer cells. Cancer Res 69 (16): 6704-6712

Liau S S, Whang E (2008) HMGAI is a molecular determinant of chemoresistance to gemcitabine in pancreatic adenocarcinoma. Clin Cancer Res 14 (5): 1470-1477

Lu D Y, Tang C H, Yeh W L, Wong K L, Lin C P, Chen Y H, Lai C H, Chen Y F, Leung Y M, Fu W M (2009) SDF-Ialpha up-regulates interleukin-6 through CXCR4, PI3K1Akt, ERK, and NFkappaB-dependent pathway in microglia. Eur J Pharmacol 613 (1-3): 146-154

Madrid L V, Wang C Y, Guttridge D C, Schottelius A J, Baldwin A S, Jr., Mayo M W (2000) Akt suppresses apoptosis by stimulating the transactivation potential of the RelAlp65 subunit of NFkappaB. Mol Cell Biol 20 (5): 1626-1638

Marchesi F, Monti P, Leone B E, Zerbi A, Vecchi A, Piemonti L, Mantovani A, Allavena P (2004) Increased survival, proliferation, and migration in metastatic human pancreatic tumor cells expressing functional CXCR4. Cancer Res 64 (22): 8420-8427

Marechal R, Demetter P, Nagy N, Berton A, Decaestecker C, Polus M, Closset J, Deviere J, Salmon I, Van Laethem J L (2009) High expression of CXCR4 may predict poor survival in resected pancreatic adenocarcinoma. Br J Cancer 100 (9): 1444-1451

Marlow R, Strickland P, Lee J S, Wu X, Pebenito M, Binnewies M. Le E K, Moran A, Macias H, Cardiff R D, Sukumar S, Hinck L (2008) SLITs suppress tumor growth in vivo by silencing Sdfl/Cxcr4 within breast epithelium. Cancer Res 68 (19): 7819-7827

Matsuo Y, Ochi N, Sawai H, Yasuda A, Takahashi H, Funahashi H, Takeyama H, Tong Z, Guha S (2009) CXCL8/IL-8 and CXCL12/SDF-Ialpha co-operatively promote invasiveness and angiogenesis in pancreatic cancer. Int J Cancer 124 (4): 853-861

Middleton G, Ghaneh P, Costello E, Greenhalf W, Neoptolemos J P (2008) New treatment options for advanced pancreatic cancer. Expert Rev Gastroenterol Hepatol 2 (5): 673-696

Monick M M, Carter A B, Robeff P K, Flaherty D M, Peterson M W, Hunninghake G W (2001) Lipopolysaccharide activates Akt in human alveolar macrophages resulting in nuclear accumulation and transcriptional activity of beta-catenin. J Immunol 166 (7): 4713-4720

Mori T, Doi R, Koizumi M, Toyoda E, Ito D, Kami K, Masui T, Fujimoto K, Tamamura H, Hiramatsu K, Fujii N, Imamura M (2004) CXCR4 antagonist inhibits stromal cell-derived factor I-induced migration and invasion of human pancreatic cancer. Mol Cancer Ther 3 (1): 29-37

Olive K P, Jacobetz M A, Davidson C J, Gopinathan A, McIntyre D, Honess D, Madhu B, Goldgraben M A, Caldwell M E, Allard D, Frese K K, Denicola G, Feig C, Combs C, Winter S P, Ireland-Zecchini H, Reichelt S, Howat W J, Chang A, Dhara M, Wang L, Ruckert F, Grutzmann R, Pilarsky C, Izeradjene K, Hingorani S R, Huang P, Davies S E, Plunkett W, Egorin M, Hruban R H, Whitebread N, McGovern K, Adams J, Iacobuzio-Donahue C, Griffiths J, Tuveson D A (2009) Inhibition of Hedgehog signaling enhances delivery of chemotherapy in a mouse model of pancreatic cancer. Science 324 (5933): 1457-1461

Ozes O N, Mayo L D, Gustin J A, Pfeffer S R, Pfeffer L M, Donner D B (1999) NF-kappaB activation by tumour necrosis factor requires the Akt serine-threonine kinase. Nature 401 (6748):82-85

Pei H, Li L, Fridley B L, Jenkins G D, Kalari K R, Lingle W, Petersen G, Lou Z, Wang L (2009) FKBP51 affects cancer cell response to chemotherapy by negatively regulating Akt. Cancer Cell 16 (3): 259-266

Rejiba S, Bigand C, Parmentier C, Hajri A (2009) Gemcitabine-based chemogene therapy for pancreatic cancer using Ad-dCK::UMK GDEPT and TSIRR siRNA strategies. Neoplasia 11 (7):637-650

Romashkova J A, Makarov S S (1999) NF-kappaB is a target of AKT in anti-apoptotic PDGF signalling. Nature 401 (6748): 86-90

Rozengurt E (2007) Mitogenic signaling pathways induced by G protein-coupled receptors. J Cell Physiol 213 (3): 589-602

Saur D, Seidler B, Schneider G, Algul H, Beck R, Senekowitsch-Schmidtke R, Schwaiger M, Schmid R M (2005) CXCR4 expression increases liver and lung metastasis in a mouse model of pancreatic cancer. Gastroenterology 129 (4): 1237-1250

Scheid M P, Duronio V (1998) Dissociation of cytokine-induced phosphorylation of Bad and activation of PKB/akt: involvement of MEK upstream of Bad phosphorylation. Proc Natl Acad Sci USA 95 (13): 7439-7444

Shah A N, Summy I M, Zhang I, Park S I, Parikh N U, Gallick G E (2007) Development and characterization of gemcitabine-resistant pancreatic tumor cells. Ann Surg Oncol 14 (1 2): 3629-3637

Shen X, Artinyan A, Jackson D, Thomas R M, Lowy A M, Kim I (2010) Chemokine receptor CXCR4 enhances proliferation in pancreatic cancer cells through AKT and ERK dependent pathways. Pancreas 39 (1): 81-87

Sheridan C, Brumatti G, Martin S I (2008) Oncogenic B-RafV600E inhibits apoptosis and promotes ERK-dependent inactivation of Bad and Bim. J Biol Chem 283 (32): 22128-22135

Singh A P, Moniaux N, Chauhan S C, Meza I L, Batra S K (2004) Inhibition of MUC4 expression suppresses pancreatic tumor cell growth and metastasis. Cancer Res 64 (2): 622-630

Singh S, Sadanandam A, Nannuru K C, Vamey M L, Mayer-Ezell R, Bond R, Singh R K (2009) Small-molecule antagonists for CXCR2 and CXCRI inhibit human melanoma growth by decreasing tumor cell proliferation, survival, and angiogenesis. Clin Cancer Res 15 (7): 2380-2386

Singh S, Sadanandam A, Singh R K (2007) Chemokines in tumor angiogenesis and metastasis. Cancer Metastasis Rev 26 (3-4): 453-467

Sizemore N, Leung S, Stark G R (1999) Activation of phosphatidylinositol 3-kinase in response to interleukin-1 leads to phosphorylation and activation of the NF-kappaB p65IReiA subunit. Mol Cell Biol 19 (7): 4798-4805

Thomas R M, Kim I, Revelo-Penafiel M P, Angel R, Dawson D W, Lowy A M (2008) The chemokine receptor CXCR4 is expressed in pancreatic intraepithelial neoplasia. Gut 57 (11): 1555-1560

Wang S I, Gao Y, Chen H, Kong R, Liang H C, Pan S H, Xue D B, Bai X W, Sun B (2010) Dihydroartemisinin inactivates NF-kappaB and potentiates the anti-tumor effect of gemcitabine on pancreatic cancer both in vitro and in vivo. Cancer Lett 293 (1): 99-108

Wang Z, Li Y, Kong D, Banerjee S, Ahmad A, Azmi A S, Ali S, Abbruzzese J L, Gallick G E, Sarkar F H (2009) Acquisition of epithelial-mesenchymal transition phenotype of gemcitabine resistant pancreatic cancer cells is linked with activation of the notch signaling pathway. Cancer Res 69 (6): 2400-2407

Wong H H, Lemoine N R (2009) Pancreatic cancer: molecular pathogenesis and new therapeutic targets. Nat Rev Gastroenterol Hepatol 6 (7): 412-422

Yasumoto K, Koizumi K, Kawashima A, Saitoh Y, Arita Y, Shinohara K, Minami T, Nakayama T, Sakurai H, Takahashi Y, Yoshie O, Saiki I (2006) Role of the CXCL12/CXCR4 axis in peritoneal carcinomatosis of gastric cancer. Cancer Res 66 (4): 2181-2187

Yokoi K, Fidler I J (2004) Hypoxia increases resistance of human pancreatic cancer cells to apoptosis induced by gemcitabine. Clin Cancer Res 10 (7): 2299-2306

Zhao Y, Shen S, Guo J, Chen H, Greenblatt D Y, Kleeff J, Liao Q, Chen G, Friess H, Leung P S (2006) Mitogen-activated protein kinases and chemoresistance in pancreatic cancer cells. J Surg Res 136 (2): 325-335

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

What is claimed is:

1. A method of reducing growth of a pancreatic tumor cell having CXCL12-mediated resistance to a chemotherapeutic agent comprising gemcitabine, wherein the cell has been contacted with the chemotherapeutic agent, said method comprising:
    reducing CXCL12-mediated resistance to said chemotherapeutic agent by:
        contacting the tumor cell with a sufficient amount of a CXCR4 antagonist selected from the group consisting of Plerixafor (AMD3100), BKT140, CTCE-9908, KRH-2731, TC14012, KRH-3955, and AMD070 to reduce said CXCL12-mediated resistance to said chemotherapeutic agent, or
        reducing the expression of a nucleic acid encoding CXCR4 in the tumor cell to a level sufficient to reduce said CXCL12-mediated resistance to said chemotherapeutic agent; and
    contacting the tumor cell with an effective amount of the chemotherapeutic agent, wherein the effective amount of the chemotherapeutic agent is less than the effective amount of the chemotherapeutic agent to reduce growth of a pancreatic tumor cell in which CXCL12-mediated resistance to said chemotherapeutic agent has not been reduced.

2. The method of claim 1, wherein reducing CXCL12-mediated resistance to said chemotherapeutic agent comprises contacting the tumor cell with a sufficient amount of a CXCR4 antagonist selected from the group consisting of Plerixafor (AMD3100), BKT140, CTCE-9908, KRH-2731, TC14012, KRH-3955, and AMD070.

3. The method of claim 2, wherein the CXCR4 antagonist comprises Plerixafor (AMD3100).

4. The method of claim 1, wherein reducing CXCL12-mediated resistance comprises reducing the expression of a nucleic acid encoding CXCR4.

5. The method of claim 4, wherein reducing the expression of a nucleic acid encoding CXCR4 comprises contacting the tumor cell with a nucleic acid selected from the group consisting of an antisense RNA, siRNA and ribozyme.

6. The method of claim 1, wherein the tumor cell is selected from the group consisting of CFPAC-1, AsPc-1, SW1990, Colo-357, MiaPaCa, Panc1, Panc02.37, Panc10.05, BxPC3, Panc02.03, HPAF-II, and CaPan-1.

7. The method of claim 1, wherein the tumor cell comprises a mammalian tumor cell.

8. The method of claim 1, wherein the tumor cell comprises a human tumor cell.

9. A method of enhancing chemotherapeutic agent-induced apoptosis in a pancreatic tumor cell having CXCL12-mediated inhibition of chemotherapeutic agent-induced apoptosis, wherein the cell has been contacted with the chemotherapeutic agent comprising gemcitabine, said method comprising:

reducing CXCL12-mediated inhibition of chemotherapeutic agent-induced apoptosis by:
  contacting the tumor cell with a sufficient amount of a CXCR4 antagonist selected from the group consisting of Plerixafor (AMD3100), BKT140, CTCE-9908, KRH-2731, TC14012, KRH-3955, and AMD070 to reduce CXCL12-mediated inhibition of chemotherapeutic drug-induced apoptosis, or
  reducing the expression of a nucleic acid encoding CXCR4 in the tumor cell to level sufficient to reduce CXCL12-mediated inhibition of chemotherapeutic agent-induced apoptosis; and
contacting the tumor cell with an effective amount of the chemotherapeutic agent, wherein the effective amount of the chemotherapeutic agent is less than the effective amount of the chemotherapeutic agent to enhance chemotherapeutic agent-induced apoptosis of a pancreatic tumor cell in which CXCL12-mediated inhibition of chemotherapeutic agent-induced apoptosis has not been reduced.

10. The method of claim 9, wherein reducing CXCL12-mediated inhibition of chemotherapeutic agent-induced apoptosis comprises contacting the tumor cell with a CXCR4 antagonist selected from the group consisting of Plerixafor (AMD3100), BKT140, CTCE-9908, KRH-2731, TC14012, KRH-3955, and AMD070.

11. The method of claim 10, wherein the CXCR4 antagonist comprises Plerixafor (AMD3100).

12. The method of claim 9, wherein reducing CXCL12-mediated inhibition of chemotherapeutic agent-induced apoptosis comprises reducing the expression of a nucleic acid encoding CXCR4.

13. The method of claim 12, wherein reducing the expression of a nucleic acid encoding CXCR4 comprises contacting the tumor cell with a nucleic acid selected from the group consisting of an antisense RNA, siRNA and ribozyme.

14. The method of claim 9, wherein the tumor cell is selected from the group consisting of CFPAC-1, AsPc-1, SW1990, Colo-357, MiaPaCa, Panc1, Panc02.37, Panc10.05, BxPC3, Panc02.03, HPAF-II, and CaPan-1.

15. The method of claim 9, wherein the tumor cell comprises a mammalian tumor cell.

16. The method of claim 9, wherein the tumor cell comprises a human tumor cell.

* * * * *

```
                        SEQUENCE LISTING

<160> NUMBER OF SEQ ID NOS: 11

<210> SEQ ID NO 1
<211> LENGTH: 14
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: (1)...(1)
<223> OTHER INFORMATION: Xaa=4-fluorobenzoyl-arginine
<220> FEATURE:
<221> NAME/KEY: VARIANT
<222> LOCATION: (3)...(3)
<223> OTHER INFORMATION: Xaa=3- ((2-naphthyl) alanine
<220> FEATURE:
<221> NAME/KEY: VARIANT
<222> LOCATION: (6)...(6)
<223> OTHER INFORMATION: Xaa=citrulline
<220> FEATURE:
<221> NAME/KEY: VARIANT
<222> LOCATION: (8)...(8)
<223> OTHER INFORMATION: Xaa=D-lysine
<220> FEATURE:
<221> NAME/KEY: VARIANT
<222> LOCATION: (12)...(12)
<223> OTHER INFORMATION: Xaa=citrulline
<220> FEATURE:
<221> NAME/KEY: VARIANT
<222> LOCATION: (14)...(14)
<223> OTHER INFORMATION: Xaa=C' AMIDATED ARGININE

<400> SEQUENCE: 1

Xaa Arg Xaa Cys Tyr Xaa Lys Xaa Pro Tyr Arg Xaa Cys Xaa
 1               5                  10

<210> SEQ ID NO 2
<211> LENGTH: 14
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: (3)...(3)
<223> OTHER INFORMATION: Xaa=3- ((2-naphthyl) alanine
<220> FEATURE:
<221> NAME/KEY: VARIANT
<222> LOCATION: (6)...(6)
<223> OTHER INFORMATION: Xaa=citrulline
<220> FEATURE:
<221> NAME/KEY: VARIANT
```

```
<222> LOCATION: (8)...(8)
<223> OTHER INFORMATION: Xaa=D-citrulline
<220> FEATURE:
<221> NAME/KEY: VARIANT
<222> LOCATION: (12)...(12)
<223> OTHER INFORMATION: Xaa=citrulline
<220> FEATURE:
<221> NAME/KEY: VARIANT
<222> LOCATION: (14)...(14)
<223> OTHER INFORMATION: Xaa=C' AMIDATED Arginine

<400> SEQUENCE: 2

Arg Arg Xaa Cys Tyr Xaa Lys Xaa Pro Tyr Arg Xaa Cys Xaa
 1               5                  10

<210> SEQ ID NO 3
<211> LENGTH: 1912
<212> TYPE: DNA
<213> ORGANISM: Homo Sapiens
<220> FEATURE:
<223> OTHER INFORMATION: CXCR-4 mRNA transcript variant 1

<400> SEQUENCE: 3
ttttttttct tccctctagt gggcggggca gaggagttag ccaagatgtg actttgaaac      60
cctcagcgtc tcagtgccct tttgttctaa acaaagaatt ttgtaattgg ttctaccaaa     120
gaaggatata atgaagtcac tatgggaaaa gatggggagg agagttgtag gattctacat     180
taattctctt gtgcccttag cccactactt cagaatttcc tgaagaaagc aagcctgaat     240 tggttttta aattgcttta aaaatttttt ttaactgggt taatgcttgc tgaattggaa     300
gtgaatgtcc attcctttgc ctcttttgca gatatacact tcagataact acaccgagga     360
aatgggctca ggggactatg actccatgaa ggaaccctgt ttccgtgaag aaaatgctaa     420
tttcaataaa atcttcctgc ccaccatcta ctccatcatc ttcttaactg gcattgtggg     480
caatggattg gtcatcctgg tcatgggtta ccagaagaaa ctgagaagca tgacggacaa     540
gtacaggctg cacctgtcag tggccgacct cctctttgtc atcacgcttc ccttctgggc     600
agttgatgcc gtggcaaact ggtactttgg gaacttccta tgcaaggcag tccatgtcat     660
ctacacagtc aacctctaca gcagtgtcct catcctggcc ttcatcagtc tggaccgcta     720
cctggccatc gtccacgcca ccaacagtca gaggccaagg aagctgttgg ctgaaaaggt     780
ggtctatgtt ggcgtctgga tccctgcccc cctgctgact attcccgact tcatctttgc     840
caacgtcagt gaggcagatg acagatatat ctgtgaccgc ttctacccca tgacttgtg     900 ggtggttgtg ttccagtttc agcacatcat ggttggcctt atcctgcctg gtattgtcat     960
cctgtcctgc tattgcatta tcatctccaa gctgtcacac tccaagggcc accagaagcg    1020
caaggccctc aagaccacag tcatcctcat cctggcttc ttcgcctgtt ggctgcctta    1080
ctacattggg atcagcatcg actccttcat cctcctggaa atcatcaagc aagggtgtga    1140
gtttgagaac actgtgcaca gtggatttc atcaccgag gccctagctt tcttccactg    1200
ttgtctgaac cccatcctct atgctttcct tggagccaaa tttaaaacct ctgcccagca    1260
cgcactcacc tctgtgagca gagggtccag cctcaagatc ctctccaaag gaaagcgagg    1320
tggacattca tctgtttcca ctgagtctga gtcttcaagt tttcactcca gctaacacag    1380
atgtaaaaga cttttttta tacgataaat aacttttttt taagttacac attttcaga    1440 tataaaagac tgaccaatat tgtacagttt ttattgcttg ttggattttt gtcttgtgtt    1500 tcttagttt ttgtgaagtt taattgactt attatataa attttttg tttcatattg    1560 atgtgtgtct aggcaggacc tgtggccaag ttcttagttg ctgtatgtct cgtggtagga    1620
```

| | |
|---|---:|
| ctgtagaaaa gggaactgaa cattccagag cgtgtagtga atcacgtaaa gctagaaatg | 1680 |
| atccccagct gtttatgcat agataatctc tccattcccg tggaacgttt ttcctgttct | 1740 |
| taagacgtga ttttgctgta gaagatggca cttataacca aagcccaaag tggtatagaa | 1800 |
| atgctggttt ttcagttttc aggagtgggt tgatttcagc acctacagtg tacagtcttg | 1860 |
| tattaagttg ttaataaaag tacatgttaa acttaaaaaa aaaaaaaaaa aa | 1912 |

<210> SEQ ID NO 4
<211> LENGTH: 1940
<212> TYPE: DNA
<213> ORGANISM: Homo Sapiens
<220> FEATURE:
<223> OTHER INFORMATION: CXCL12 mRNA transcript

<400> SEQUENCE: 4

| | |
|---|---:|
| gccgcacttt cactctccgt cagccgcatt gcccgctcgg cgtccggccc ccgacccgcg | 60 |
| ctcgtccgcc cgcccgcccg cccgcccgcg ccatgaacgc caaggtcgtg gtcgtgctgg | 120 |
| tcctcgtgct gaccgcgctc tgcctcagcg acgggaagcc cgtcagcctg agctacagat | 180 |
| gcccatgccg attcttcgaa agccatgttg ccagagccaa cgtcaagcat ctcaaaattc | 240 |
| tcaacactcc aaactgtgcc cttcagattg tagcccggct gaagaacaac aacagacaag | 300 |
| tgtgcattga cccgaagcta aagtggattc aggagtacct ggagaaagct ttaaacaagt | 360 |
| aagcacaaca gccaaaaagg actttccgct agacccactc gaggaaaact aaaaccttgt | 420 |
| gagagatgaa agggcaaaga cgtgggggag ggggccttaa ccatgaggac caggtgtgtg | 480 |
| tgtggggtgg gcacattgat ctgggatcgg gcctgaggtt tgccagcatt tagaccctgc | 540 |
| atttatagca tacggtatga tattgcagct tatattcatc catgccctgt acctgtgcac | 600 |
| gttggaactt ttattactgg ggtttttcta agaaagaaat tgtattatca acagcatttt | 660 |
| caagcagtta gttccttcat gatcatcaca atcatcatca ttctcattct cattttttaa | 720 |
| atcaacgagt acttcaagat ctgaatttgg cttgtttgga gcatctcctc tgctcccctg | 780 |
| gggagtctgg gcacagtcag gtggtggctt aacagggagc tggaaaaagt gtcctttctt | 840 |
| cagacactga ggctcccgca gcagcgcccc tcccaagagg aaggcctctg tggcactcag | 900 |
| ataccgactg gggctgggcg ccgccactgc ctttcacctcc tctttcaacc tcagtgattg | 960 |
| gctctgtggg ctccatgtag aagccactat tactgggact gtgctcagag acccctctcc | 1020 |
| cagctattcc tactctctcc ccgactccga gagcatgctt aatcttgctt ctgcttctca | 1080 |
| tttctgtagc ctgatcagcg ccgcaccagc cgggaagagg gtgattgctg gggctcgtgc | 1140 |
| cctgcatccc tctcctccca gggcctgccc cacagctcgg gccctctgtg agatccgtct | 1200 |
| ttggcctcct ccagaatgga gctggccctc tcctggggat gtgtaatggt cccctgctt | 1260 |
| acccgcaaaa gacaagtctt tacagaatca aatgcaattt taaatctgag agctcgcttt | 1320 |
| gagtgactgg gttttgtgat tgcctctgaa gcctatgtat gccatggagg cactaacaaa | 1380 |
| ctctgaggtt tccgaaatca gaagcgaaaa aatcagtgaa taaaccatca tcttgccact | 1440 |
| accccctcct gaagccacag cagggtttca ggttccaatc agaactgttg gcaaggtgac | 1500 |
| atttccatgc ataaatgcga tccacagaag gtcctggtgg tatttgtaac ttttttgcaag | 1560 |
| gcattttttt atatatattt ttgtgcacat ttttttttac gtttctttag aaaacaaatg | 1620 |
| tatttcaaaa tatatttata gtcgaacaat tcatatattt gaagtggagc catatgaatg | 1680 |
| tcagtagttt atacttctct attatctcaa actactggca atttgtaaag aaatatatat | 1740 |

```
gatatataaa tgtgattgca gcttttcaat gttagccaca gtgtattttt tcacttgtac    1800
taaaattgta tcaaatgtga cattatatgc actagcaata aaatgctaat tgtttcatgg    1860
tataaacgtc ctactgtatg tgggaattta tttacctgaa ataaaattca ttagttgtta    1920
gtgatggagc ttaaaaaaaa                                                1940
```

```
<210> SEQ ID NO 5
<211> LENGTH: 31
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: (23)...(23)
<223> OTHER INFORMATION: Xaa=Gln cyclized to position 27
<220> FEATURE:
<221> NAME/KEY: VARIANT
<222> LOCATION: (27)...(27)
<223> OTHER INFORMATION: Xaa=Glu cyclized to position 23

<400> SEQUENCE: 5

Lys Pro Val Ser Leu Ser Tyr Arg Ala Pro Phe Arg Phe Phe Gly Gly
 1               5                  10                  15

Gly Gly Leu Lys Trp Ile Xaa Glu Tyr Leu Xaa Lys Ala Leu Asn
            20                  25                  30

<210> SEQ ID NO 6
<211> LENGTH: 14
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: (3)...(3)
<223> OTHER INFORMATION: Xaa=3- ((2-naphthyl) alanine
<220> FEATURE:
<221> NAME/KEY: VARIANT
<222> LOCATION: (6)...(6)
<223> OTHER INFORMATION: Xaa=citrulline
<220> FEATURE:
<221> NAME/KEY: VARIANT
<222> LOCATION: (8)...(8)
<223> OTHER INFORMATION: Xaa=D-lysine
<220> FEATURE:
<221> NAME/KEY: VARIANT
<222> LOCATION: (12)...(12)
<223> OTHER INFORMATION: Xaa=citrulline
<220> FEATURE:
<221> NAME/KEY: VARIANT
<222> LOCATION: (14)...(14)
<223> OTHER INFORMATION: Xaa=C' AMIDATED Arginine

<400> SEQUENCE: 6

Arg Arg Xaa Cys Tyr Xaa Lys Xaa Pro Tyr Arg Xaa Cys Xaa
 1               5                  10

<210> SEQ ID NO 7
<211> LENGTH: 17
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: (9)...(9)
<223> OTHER INFORMATION: Xaa=Lys - CONH-2

<400> SEQUENCE: 7
```

Lys Gly Val Ser Leu Ser Tyr Arg Xaa Arg Tyr Ser Leu Ser Val Gly
 1               5                  10                  15

Lys

<210> SEQ ID NO 8
<211> LENGTH: 3545
<212> TYPE: DNA
<213> ORGANISM: Homo Sapiens
<220> FEATURE:
<223> OTHER INFORMATION: CXCL12, variant 2

<400> SEQUENCE: 8

| | | | | |
|---|---|---|---|---|
| gccgcacttt | cactctccgt | cagccgcatt | gcccgctcgg | cgtccggccc | ccgacccgcg | 60 |
| ctcgtccgcc | cgcccgcccg | cccgcccgcg | ccatgaacgc | caaggtcgtg | gtcgtgctgg | 120 |
| tcctcgtgct | gaccgcgctc | tgcctcagcg | acgggaagcc | cgtcagcctg | agctacagat | 180 |
| gcccatgccg | attcttcgaa | agccatgttg | ccagagccaa | cgtcaagcat | ctcaaaattc | 240 |
| tcaacactcc | aaactgtgcc | cttcagattg | tagcccggct | gaagaacaac | aacagacaag | 300 |
| tgtgcattga | cccgaagcta | aagtggattc | aggagtacct | ggagaaagct | taaacaaga | 360 |
| ggttcaagat | gtgagagggt | cagacgcctg | aggaacccct | tacagtaggag | cccagctctg | 420 |
| aaaccagtgt | tagggaaggg | cctgccacag | cctcccctgc | cagggcaggg | ccccaggcat | 480 |
| tgccaagggc | tttgttttgc | acactttgcc | atattttcac | catttgatta | tgtagcaaaa | 540 |
| tacatgacat | ttattttca | tttagtttga | ttattcagtg | tcactggcga | cacgtagcag | 600 |
| cttagactaa | ggccattatt | gtacttgcct | tattagagtg | tctttccacg | gagccactcc | 660 |
| tctgactcag | ggctcctggg | ttttgtattc | tctgagctgt | gcaggtgggg | agactgggct | 720 |
| gagggagcct | ggccccatgg | tcagccctag | ggtggagagc | caccaagagg | gacgcctggg | 780 |
| ggtgccagga | ccagtcaacc | tgggcaaagc | ctagtgaagg | cttctctctg | tgggatggga | 840 |
| tggtggaggg | ccacatggga | ggctcacccc | cttctccatc | cacatgggag | ccgggtctgc | 900 |
| ctcttctggg | agggcagcag | ggctaccctg | agctgaggca | gcagtgtgag | gccagggcag | 960 |
| agtgagaccc | agccctcatc | ccgagcacct | ccacatcctc | cacgttctgc | tcatcattct | 1020 |
| ctgtctcatc | catcatcatg | tgtgtccacg | actgtctcca | tggccccgca | aaaggactct | 1080 |
| caggaccaaa | gctttcatgt | aaactgtgca | ccaagcagga | aatgaaaatg | tcttgtgtta | 1140 |
| cctgaaaaca | ctgtgcacat | ctgtgtcttg | tttggaatat | tgtccattgt | ccaatcctat | 1200 |
| gtttttgttc | aaagccagcg | tcctcctctg | tgaccaatgt | cttgatgcat | gcactgttcc | 1260 |
| ccctgtgcag | ccgctgagcg | aggagatgct | ccttgggccc | tttgagtgca | gtcctgatca | 1320 |
| gagccgtggt | cctttggggt | gaactacctt | ggttccccca | ctgatcacaa | aaacatggtg | 1380 |
| ggtccatggg | cagagcccaa | gggaattcgg | tgtgcaccag | ggttgacccc | agaggattgc | 1440 |
| tgccccatca | gtgctccctc | acatgtcagt | accttcaaac | tagggccaag | cccagcactg | 1500 |
| cttgaggaaa | acaagcattc | acaacttgtt | tttggttttt | aaaacccagt | ccacaaaata | 1560 |
| accaatcctg | gacatgaaga | ttctttccca | attcacatct | aacctcatct | tcttcaccat | 1620 |
| ttggcaatgc | catcatctcc | tgccttcctc | ctgggccctc | tctgctctgc | gtgtcacctg | 1680 |
| tgcttcgggc | ccttcccaca | ggacatttct | ctaagagaac | aatgtgctat | gtgaagagta | 1740 |
| agtcaacctg | cctgacattt | ggagtgttcc | ccttccactg | agggcagtcg | atagagctgt | 1800 |
| attaagccac | ttaaaatgtt | cacttttgac | aaaggcaagc | acttgtgggt | ttttgttttg | 1860 |
| tttttcattc | agtcttacga | atacttttgc | cctttgatta | aagactccag | ttaaaaaaaa | 1920 |

| | |
|---|---|
| ttttaatgaa gaaagtggaa acaaggaag tcaaagcaag gaaactatgt aacatgtagg | 1980 |
| aagtaggaag taaattatag tgatgtaatc ttgaattgta actgttcttg aatttaataa | 2040 |
| tctgtagggt aattagtaac atgtgttaag tattttcata agtatttcaa attggagctt | 2100 |
| catggcagaa ggcaaaccca tcaacaaaaa ttgtcccctta acaaaaatt aaaatcctca | 2160 |
| atccagctat gttatattga aaaaatagag cctgagggat ctttactagt tataaagata | 2220 |
| cagaactctt tcaaaacctt ttgaaattaa cctctcacta taccagtata attgagtttt | 2280 |
| cagtggggca gtcattatcc aggtaatcca agatatttta aaatctgtca cgtagaactt | 2340 |
| ggatgtacct gcccccaatc catgaaccaa gaccattgaa ttcttggttg aggaaacaaa | 2400 |
| catgacccta atcttgact acagtcagga aaggaatcat ttctatttct cctccatggg | 2460 |
| agaaaataga taagagtaga aactgcaggg aaaattattt gcataacaat tcctctacta | 2520 |
| acaatcagct ccttcctgga gactgcccag ctaaagcaat atgcatttaa atacagtctt | 2580 |
| ccatttgcaa gggaaaagtc tcttgtaatc cgaatctctt tttgctttcg aactgctagt | 2640 |
| caagtgcgtc cacgagctgt ttactaggga tccctcatct gtccctccgg gacctggtgc | 2700 |
| tgcctctacc tgacactccc ttgggctccc tgtaacctct tcagaggccc tcgctgccag | 2760 |
| ctctgtatca ggacccagag gaaggggcca gaggctcgtt gactggctgt gtgttgggat | 2820 |
| tgagtctgtg ccacgtgttt gtgctgtggt gtgtcccccct ctgtccaggc actgagatac | 2880 |
| cagcgaggag gctccagagg gcactctgct tgttattaga gattacctcc tgagaaaaaa | 2940 |
| ggttccgctt ggagcagagg ggctgaatag cagaaggttg cacctccccc aaccttagat | 3000 |
| gttctaagtc tttccattgg atctcattgg acccttccat ggtgtgatcg tctgactggt | 3060 |
| gttatcaccg tgggctccct gactgggagt tgatcgcctt cccaggtgc taccccttt | 3120 |
| tccagctgga tgagaatttg agtgctctga tccctctaca gagcttccct gactcattct | 3180 |
| gaaggagccc cattcctggg aaatattccc tagaaacttc caaatcccct aagcagacca | 3240 |
| ctgataaaac catgtagaaa atttgttatt ttgcaacctc gctggactct cagtctctga | 3300 |
| gcagtgaatg attcagtgtt aaatgtgatg aatactgtat tttgtattgt ttcaattgca | 3360 |
| tctcccagat aatgtgaaaa tggtccagga gaaggccaat tcctatacgc agcgtgcttt | 3420 |
| aaaaaataaa taagaaacaa ctctttgaga aacaacaatt tctactttga agtcatacca | 3480 |
| atgaaaaaat gtatatgcac ttataatttt cctaataaag ttctgtactc aaatgtagcc | 3540 |
| accaa | 3545 |

<210> SEQ ID NO 9
<211> LENGTH: 524
<212> TYPE: DNA
<213> ORGANISM: Homo Sapiens
<220> FEATURE:
<223> OTHER INFORMATION: CXCL12, variant 3

<400> SEQUENCE: 9

| | |
|---|---|
| gccgcacttt cactctccgt cagccgcatt gcccgctcgg cgtccggccc ccgacccgcg | 60 |
| ctcgtccgcc cgcccgcccg cccgcccgcg ccatgaacgc caaggtcgtg gtcgtgctgg | 120 |
| tcctcgtgct gaccgcgctc tgcctcagcg acgggaagcc cgtcagcctg agctacagat | 180 |
| gcccatgccg attcttcgaa agccatgttg ccagagccaa cgtcaagcat ctcaaaattc | 240 |
| tcaacactcc aaactgtgcc cttcagattg tagcccggct gaagaacaac aacagacaag | 300 |
| tgtgcattga cccgaagcta agtggattc aggagtacct ggagaaagct ttaaacaagg | 360 |
| ggcgcagaga agaaaaagtg gggaaaaaag aaaagatagg aaaaaagaag cgacagaaga | 420 |

| | |
|---|---|
| agagaaaggc tgcccagaaa aggaaaaact agttatctgc cacctcgaga tggaccacag | 480 |
| ttcacttgct ctcggcgctt tgtaaatttg ctcgatcctc ctcc | 524 |

<210> SEQ ID NO 10
<211> LENGTH: 1209
<212> TYPE: DNA
<213> ORGANISM: Homo Sapiens
<220> FEATURE:
<223> OTHER INFORMATION: CXCL12, variant 4

<400> SEQUENCE: 10

| | |
|---|---|
| gccgcacttt cactctccgt cagccgcatt gcccgctcgg cgtccggccc ccgacccgcg | 60 |
| ctcgtccgcc cgcccgcccg cccgcccgcg ccatgaacgc caaggtcgtg gtcgtgctgg | 120 |
| tcctcgtgct gaccgcgctc tgcctcagcg acgggaagcc cgtcagcctg agctacagat | 180 |
| gcccatgccg attcttcgaa agccatgttg ccagagccaa cgtcaagcat ctcaaaattc | 240 |
| tcaacactcc aaactgtgcc cttcagattg tagcccggct gaagaacaac aacagacaag | 300 |
| tgtgcattga cccgaagcta agtggattc aggagtacct ggagaaagct ttaaacaacc | 360 |
| tgatcagcgc cgcaccagcc gggaagaggg tgattgctgg ggctcgtgcc ctgcatccct | 420 |
| ctcctcccag ggcctgcccc acagctcggg ccctctgtga tccgtctt tggcctcctc | 480 |
| cagaatggag ctggccctct cctggggatg tgtaatggtc ccctgcttaa cccgcaaaag | 540 |
| acaagtcttt acagaatcaa atgcaatttt aaatctgaga gctcgctttg agtgactggg | 600 |
| ttttgtgatt gcctctgaag cctatgtatg ccatggaggc actaacaaac tctgaggttt | 660 |
| ccgaaatcag aagcgaaaaa atcagtgaat aaaccatcat cttgccacta cccctcctg | 720 |
| aagccacagc agggtttcag gttccaatca gaactgttgg caaggtgaca tttccatgca | 780 |
| taaatgcgat ccacagaagg tcctggtggt atttgtaact ttttgcaagg catttttta | 840 |
| tatatatttt tgtgcacatt ttttttacg tttctttaga aaacaaatgt atttcaaaat | 900 |
| atatttatag tcgaacaatt catatatttg aagtggagcc atatgaatgt cagtagttta | 960 |
| tacttctcta ttatctcaaa ctactggcaa tttgtaaaga aatatatatg atatataaat | 1020 |
| gtgattgcag cttttcaatg ttagccacag tgtatttttt cacttgtact aaaattgtat | 1080 |
| caaatgtgac attatatgca ctagcaataa aatgctaatt gtttcatggt ataaacgtcc | 1140 |
| tactgtatgt gggaatttat ttacctgaaa taaaattcat tagttgttag tgatggagct | 1200 |
| taaaaaaaa | 1209 |

<210> SEQ ID NO 11
<211> LENGTH: 1691
<212> TYPE: DNA
<213> ORGANISM: Homo Sapiens
<220> FEATURE:
<223> OTHER INFORMATION: CXCR-4

<400> SEQUENCE: 11

| | |
|---|---|
| aacttcagtt tgttggctgc ggcagcaggt agcaaagtga cgccgagggc ctgagtgctc | 60 |
| cagtagccac cgcatctgga gaaccagcgg ttaccatgga ggggatcagt atatacactt | 120 |
| cagataacta caccgaggaa atgggctcag gggactatga ctccatgaag gaaccctgtt | 180 |
| tccgtgaaga aaatgctaat ttcaataaaa tcttcctgcc caccatctac tccatcatct | 240 |
| tcttaactgg cattgtgggc aatgcattgg tcatcctggt catgggttac cagaagaaac | 300 |
| tgagaagcat gacggacaag tacaggctgc acctgtcagt ggccgacctc ctctttgtca | 360 |

-continued

```
tcacgcttcc cttctgggca gttgatgccg tggcaaactg gtactttggg aacttcctat    420
gcaaggcagt ccatgtcatc tacacagtca acctctacag cagtgtcctc atcctggcct    480
tcatcagtct ggaccgctac ctggccatcg tccacgccac caacagtcag aggccaagga    540
agctgttggc tgaaaaggtg gtctatgttg gcgtctggat ccctgccctc ctgctgacta    600
ttcccgactt catctttgcc aacgtcagtg aggcagatga cagatatatc tgtgaccgct    660
tctaccccaa tgacttgtgg gtggttgtgt tccagtttca gcacatcatg gttggcctta    720
tcctgcctgg tattgtcatc ctgtcctgct attgcattat catctccaag ctgtcacact    780
ccaagggcca ccagaagcgc aaggccctca agaccacagt catcctcatc ctggctttct    840
tcgcctgttg gctgccttac tacattggga tcagcatcga ctccttcatc ctcctggaaa    900
tcatcaagca agggtgtgag tttgagaaca ctgtgcacaa gtggatttcc atcaccgagg    960
ccctagcttt cttccactgt tgtctgaacc ccatcctcta tgctttcctt ggagccaaat   1020
ttaaaacctc tgcccagcac gcactcacct ctgtgagcag agggtccagc ctcaagatcc   1080
tctccaaagg aaagcgaggt ggacattcat ctgtttccac tgagtctgag tcttcaagtt   1140
ttcactccag ctaacacaga tgtaaaagac ttttttttat acgataaata acttttttt    1200 aagttacaca tttttcagat ataaaagact gaccaatatt gtacagtttt tattgcttgt   1260 tggattttg tcttgtgttt ctttagtttt tgtgaagttt aattgactta tttatataaa   1320
ttttttttgt ttcatattga tgtgtgtcta ggcaggacct gtggccaagt tcttagttgc   1380
tgtatgtctc gtggtaggac tgtagaaaag ggaactgaac attccagagc gtgtagtgaa   1440
tcacgtaaag ctagaaatga tccccagctg tttatgcata gataatctct ccattcccgt   1500
ggaacgtttt tcctgttctt aagacgtgat tttgctgtag aagatggcac ttataaccaa   1560
agcccaaagt ggtatagaaa tgctggtttt tcagttttca ggagtgggtt gatttcagca   1620
cctacagtgt acagtcttgt attaagttgt taataaaagt acatgttaaa cttaaaaaaa   1680 aaaaaaaaa a                                                         1691
```